(12) United States Patent
Theyssen et al.

(10) Patent No.: US 9,476,017 B2
(45) Date of Patent: Oct. 25, 2016

(54) COMPOSITIONS AND METHODS FOR CLEANING, DISINFECTING, AND SANITIZING THAT ARE EFFLUENT NEUTRAL

(71) Applicant: Diversey, Inc, Sturtevant, WI (US)

(72) Inventors: Holger Theyssen, Freinsheim (DE); Marco Haag, Goennheim (DE); Henry Von Rege, Alzey (DE); Jeff Denton, Ripley (GB); John Cornford, Klaeng (TH)

(73) Assignee: DIVERSEY, INC., Sturtevant, WI (US)

( * ) Notice: Subject to any disclaimer, the term of this patent is extended or adjusted under 35 U.S.C. 154(b) by 0 days.

(21) Appl. No.: 14/406,162

(22) PCT Filed: Jun. 7, 2013

(86) PCT No.: PCT/US2013/044781
§ 371 (c)(1),
(2) Date: Dec. 5, 2014

(87) PCT Pub. No.: WO2013/185074
PCT Pub. Date: Dec. 12, 2013

(65) Prior Publication Data
US 2015/0152364 A1 Jun. 4, 2015

Related U.S. Application Data

(60) Provisional application No. 61/656,869, filed on Jun. 7, 2012.

(51) Int. Cl.
| | | |
|---|---|---|
| *C11D 3/06* | (2006.01) |
| *C11D 7/16* | (2006.01) |
| *C11D 11/00* | (2006.01) |
| *A61L 2/18* | (2006.01) |
| *C11D 1/66* | (2006.01) |
| *C11D 3/04* | (2006.01) |
| *C11D 3/08* | (2006.01) |
| *C11D 3/20* | (2006.01) |
| *C11D 3/30* | (2006.01) |
| *C11D 3/33* | (2006.01) |
| *C11D 3/36* | (2006.01) |
| *C11D 3/37* | (2006.01) |
| *C11D 3/386* | (2006.01) |
| *C11D 3/39* | (2006.01) |
| *C11D 3/48* | (2006.01) |
| *C11D 7/06* | (2006.01) |
| *C11D 7/08* | (2006.01) |
| *C11D 7/14* | (2006.01) |
| *C11D 7/26* | (2006.01) |
| *C11D 7/32* | (2006.01) |
| *C11D 7/36* | (2006.01) |
| *C11D 3/10* | (2006.01) |
| *C11D 3/12* | (2006.01) |

(52) U.S. Cl.
CPC ............ *C11D 11/0041* (2013.01); *A23K 20/00* (2016.05); *A61L 2/186* (2013.01); *C11D 1/66* (2013.01); *C11D 3/042* (2013.01); *C11D 3/044* (2013.01); *C11D 3/046* (2013.01); *C11D 3/06* (2013.01); *C11D 3/08* (2013.01); *C11D 3/10* (2013.01); *C11D 3/1233* (2013.01); *C11D 3/2086* (2013.01); *C11D 3/30* (2013.01); *C11D 3/33* (2013.01); *C11D 3/364* (2013.01); *C11D 3/365* (2013.01); *C11D 3/373* (2013.01); *C11D 3/3707* (2013.01); *C11D 3/386* (2013.01); *C11D 3/39* (2013.01); *C11D 3/3942* (2013.01); *C11D 3/3945* (2013.01); *C11D 3/48* (2013.01); *C11D 7/06* (2013.01); *C11D 7/08* (2013.01); *C11D 7/14* (2013.01); *C11D 7/265* (2013.01); *C11D 7/3218* (2013.01); *C11D 7/36* (2013.01); *C11D 11/0076* (2013.01)

(58) Field of Classification Search
CPC ....... C11D 3/06; C11D 3/3418; C11D 3/362; C11D 11/0023; C11D 11/0064; C11D 11/007; C11D 11/0076; C11D 7/16
See application file for complete search history.

(56) References Cited

U.S. PATENT DOCUMENTS

| | | | | |
|---|---|---|---|---|
| 5,567,444 A * | 10/1996 | Hei | ......................... | A61L 2/202 134/2 |
| 5,571,446 A * | 11/1996 | Rouillard | ............. | C11D 3/3765 510/234 |
| 6,042,629 A * | 3/2000 | McGarrity | .............. | B08B 9/027 134/27 |
| 6,204,231 B1 * | 3/2001 | Patten | .................... | C11D 3/044 134/10 |
| 2005/0183744 A1 * | 8/2005 | Staub | .................... | B08B 9/0321 134/22.1 |
| 2010/0236581 A1 * | 9/2010 | Fernholz | ................. | A01J 7/022 134/26 |
| 2013/0000681 A1 * | 1/2013 | Johnson | .................... | C23G 1/02 134/22.19 |

FOREIGN PATENT DOCUMENTS

| | | |
|---|---|---|
| WO | WO-97/01288 A1 | 1/1997 |
| WO | WO-99/00025 A1 | 1/1999 |
| WO | WO-2010/009305 A2 | 1/2010 |

OTHER PUBLICATIONS

International Search Report and Written Opinion of the International Search Authority received in International Application No. PCT/US2013/044781 mailed Jun. 25, 2014, 32 pages.

* cited by examiner

*Primary Examiner* — Charles Boyer
(74) *Attorney, Agent, or Firm* — Foley & Lardner LLP

(57) ABSTRACT

Methods are provided which include a method of cleaning, sanitizing, or disinfecting, wherein the method comprises: contacting a soiled substrate with a cleaning, sanitizing, or disinfecting composition, such that at least a portion of the soil is removed from the substrate; wherein the cleaning, sanitizing, or disinfecting composition consists essentially of one or more food grade agents or a salt thereof; and wherein the method is effluent neutral.

16 Claims, 6 Drawing Sheets

COMPOSITIONS AND METHODS FOR CLEANING, DISINFECTING, AND SANITIZING THAT ARE EFFLUENT NEUTRAL

CROSS-REFERENCE TO RELATED APPLICATIONS

This application is the U.S. National Stage of International Application No. PCT/US2013/044781, with international filing date Jun. 7, 2013, which claims the benefit of and priority to U.S. Provisional Application No. 61/656,869, filed Jun. 7, 2012, the contents of which are incorporated herein by reference in their entireties and for all purposes.

FIELD

The present technology relates generally to the field of cleaning, disinfecting and sanitizing industrial equipment.

BACKGROUND

The food and beverage industries (e.g., production and serving) regularly clean and sanitize their industrial equipment to maintain product quality and ensure the public health. Production residuals that remain on industrial equipment compromise product quality and promote the growth of pathogenic microorganisms. Thus, the food and beverage industries typically clean and sanitize their industrial equipment to reduce microbial population to safe levels. Similarly, other industries that use fermentation processes to produce pharmaceuticals, cosmetics, nutritional supplements or biofuels also clean and sanitize their production equipment to maintain product quality and consistency.

Breweries, for example, routinely clean industrial equipment with solutions of caustic such as sodium hydroxide. Sodium hydroxide is inexpensive, but imperfectly suited for cleaning brewery equipment in, e.g., a clean-in-place process which contains an atmosphere of carbon dioxide because residual carbonic acid will react with the basic hydroxide to form carbonate. Further, the hydroxide must be neutralized after cleaning, and before being discharged from the industrial equipment, to minimize any impact to the environment. Thus, cleaning compositions are needed that are better suited to food and beverage industries, such as breweries, and more compatible with the environment.

SUMMARY

The present technology provides compositions and methods of cleaning, disinfecting, and sanitizing industrial equipment that are effluent neutral. Effluent neutral (e.g., effluent-free) compositions and methods yield effluents, if any, consisting essentially of water. The cleaning, disinfecting, or sanitizing compositions may be, for example, filtered or concentrated after use and the resulting effluent, if any, need not be chemically or biologically treated (e.g., sanitized, oxidized, neutralized, etc.) before being discharged into the environment and/or disposed of in a landfill. Generally, the aqueous compositions described herein are added to a soiled piece of equipment and used to clean and dislodge the soiled residues from the equipment. Once the equipment has been cleaned, and thus most or all of the soiled residues have dissolved or become suspended in the composition, the soiled composition is recovered from the equipment. Upon concentration, water from the recovered composition may be disposed of, or optionally recycled, and the resulting concentrate and/or soiled solids can be added to animal feed stocks. As such, the compositions are generally prepared from food grade ingredients that can safely be added to animal feed stocks in addition to the soiled residues that are washed away from industrial equipment. Such compositions and methods of cleaning, disinfecting, and sanitizing industrial equipment minimally impact the environment by reducing or eliminating toxic or harmful effluent discharge of spent cleaning solutions and converting an industrial waste stream into a source for animal feed.

According to one aspect, the present technology provides a method of cleaning, sanitizing, and/or disinfecting, wherein the method comprises: contacting a soiled substrate with a cleaning, sanitizing, or disinfecting composition, such that at least a portion of the soil is removed from the substrate; wherein the cleaning, sanitizing, or disinfecting composition consists of or consists essentially of one or more food grade agents or a salt thereof; and wherein the method is effluent neutral. In some embodiments, the soiled cleaning, sanitizing, or disinfecting composition is added to an animal feedstock. In some embodiments of the method, the one or more agents comprise fertilizer agents.

According to another aspect, the present technology provides a method of cleaning, sanitizing, or disinfecting, wherein the method comprises: contacting a soiled substrate with a cleaning, sanitizing, or disinfecting composition, such that at least a portion of the soil is removed from the substrate; where the cleaning, sanitizing, or disinfecting composition consists of or consists essentially of one or more agents, or a salt thereof, selected from the group consisting of hydroxide, carbonate, bicarbonate, silicate ($SiO_4^{4-}$), monoethanolamine, an enzyme, peroxy acid, hydrogen peroxide, an ethoxylated alcohol, an alkylpolyglycoside, ethyleneoxide/propylene oxide copolymer, octenylsuccinic anhydride, octenylsuccinic acid, aminotrimethylene phosphonic acid, phosphono-1,2,4-butanetricaboxylic acid, gluconic acid, a maleic acid/olefin-copolymer, polyacrylic acid, ethylene diamine tetraacetic acid (EDTA), glutamic acid diacetic acid (GLDA), methyl glycine diacetic acid (MGDA), nitrilo triacetic acid (NTA), caprylic acid, sorbic acid, alkyl ($C_{8-24}$) dibasic fatty acid, alkyl $C_{8-10}$ polyglycolic acid, glycolic acid, citric acid, lactic acid, phosphoric acid, tripolyphosphoric acid, hexametaphosphoric acid, nitric acid, sulphuric acid, methane sulphonic acid, polyalkylene glycol, lauryl dimethyl betaine, and a polydimethyl siloxane emulsion; and where the method is effluent neutral. In some embodiments, the one or more agents comprise food grade agents. In some embodiments, the method is a method of cleaning. In some embodiments, the method is a method of sanitizing. In some embodiments, the method is a method of disinfecting. In some embodiments, the method is a method of cleaning and/or sanitizing and/or disinfecting.

In some embodiments, methods are provided comprising the removal of a soiled cleaning, sanitizing, or disinfecting composition from the substrate (e.g., industrial equipment) which has been cleaned, sanitized, or disinfected. The methods may further comprise adding the soiled cleaning, sanitizing, or disinfecting composition to an animal feedstock. In some embodiments, the soil on the soiled substrate comprises a residue from grain, dairy product, alcoholic beverage, non-alcoholic beverage, fruit, vegetable, meat, animal food, soiled dish residue, an industrial fermentation (e.g., algae, a biofuel such as ethanol or biodiesel, or other fermentation product such as a pharmaceutical, nutritional supplement or cosmetic), or a combination of any two or more thereof. The term, "residue" as used herein encompasses residues derived from starting materials and byproducts.

In some embodiments of the present methods, the substrate is selected from the group consisting of a brewing apparatus for an alcoholic beverage, apparatus for producing a nonalcoholic beverage, apparatus for producing a dairy product, food-processing apparatus, industrial fermentation apparatus, algae fermentation apparatus, apparatus for producing biofuel, pharmaceutical processing apparatus, cosmetic processing apparatus, apparatus for producing a nutritional supplement, and a dish-washing apparatus. In some embodiments, the method of cleaning, sanitizing, or disinfecting comprises mechanical dish-washing.

In some embodiments of the present method, the method of cleaning, sanitizing, or disinfecting is a clean-in-place (CIP) or a sanitize-in-place (SIP) method. In some embodiments, the method is carried out under an atmosphere comprising a higher percentage of carbon dioxide than air. In some embodiments, the substrate is a brewing apparatus for an alcoholic beverage and any cleaning, sanitizing, or disinfecting composition remaining on the substrate contacts the brewed beverage. In some embodiments, the brewed beverage is beer.

According to another aspect, the present technology provides an animal feedstock comprising: animal feed; and a soiled cleaning, sanitizing, or disinfecting composition, wherein the soiled cleaning, sanitizing, or disinfecting composition consists essentially of (i) one or more food grade agents and (ii) one or more residues comprising a grain, dairy, alcoholic beverage, non-alcoholic beverage, fruit, vegetable, meat, animal food, soiled dish, industrial fermentation product, algae, biofuel, pharmaceutical, nutritional supplement, cosmetic or a combination of any two or more thereof.

DETAILED DESCRIPTION

Figure 1:
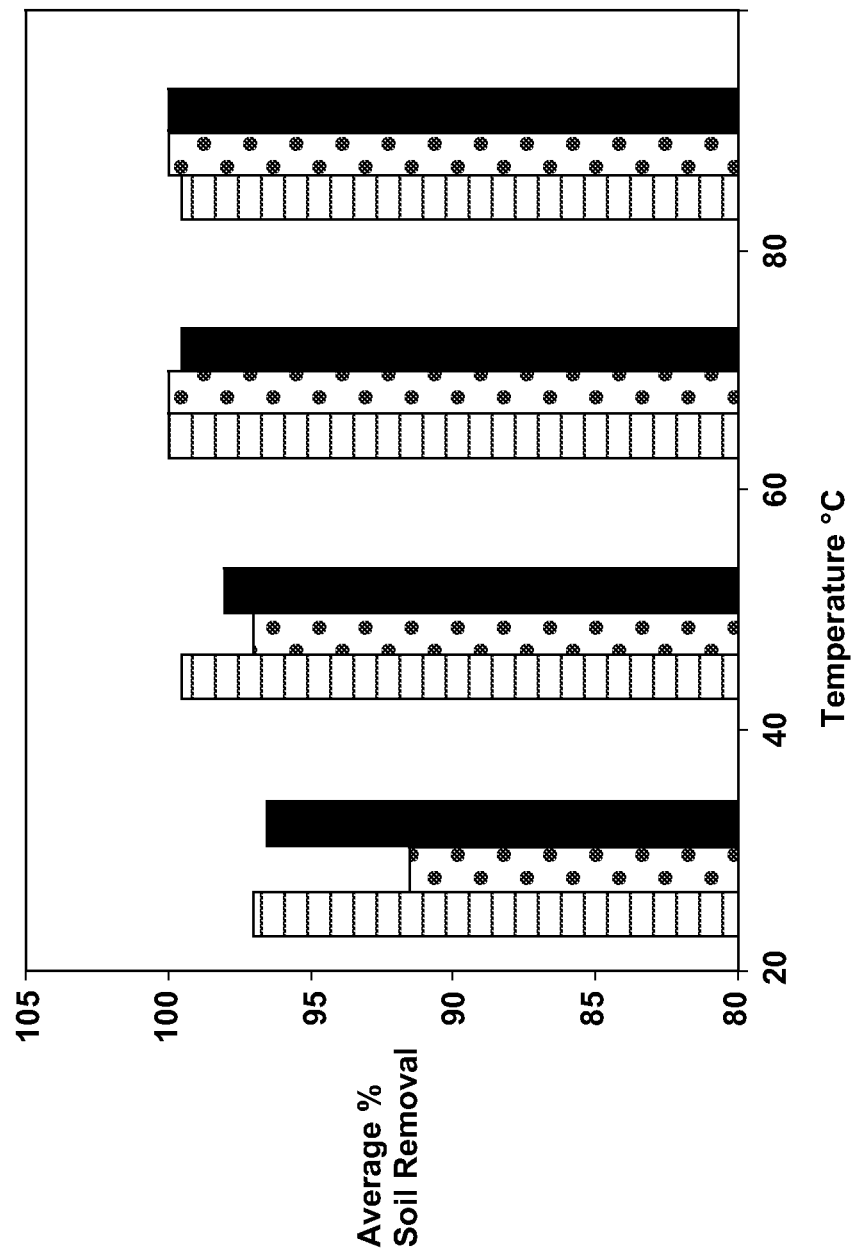
FIG. 1 provides the results of cleaning tests on stainless steel as described in Example 4. The striped bars are Formulation B; dotted bars are Formulation D; solid bars are caustic+Formulation B.
Figure 2:
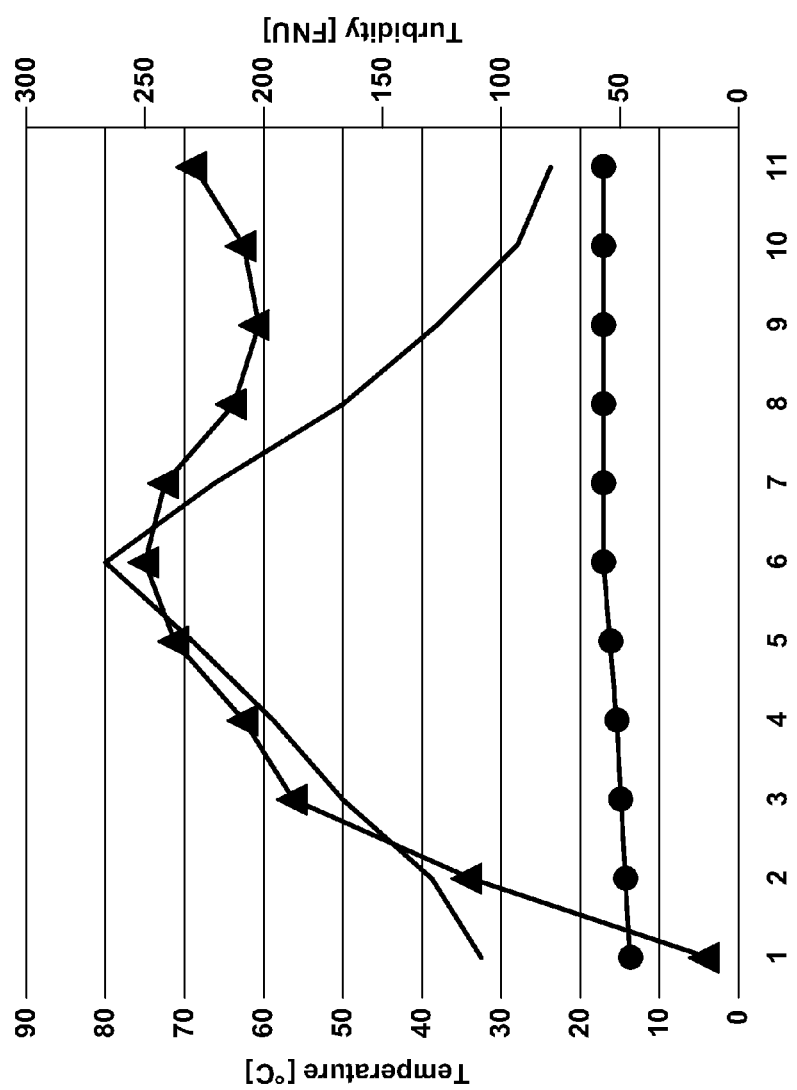
FIG. 2 provides the results of turbidity testing at various temperatures as described in Example 5. At measurement points 1-11 in FIG. 2, temperature and turbidity were measured. Straight line is turbidity temperature [° C.]; triangles are turbidity [FNU] without Formulation B ("Form B"); circles are turbidity [FNU] with 0.2% Form B.

In the following detailed description and claims, the illustrative embodiments described are not meant to be limiting. Other embodiments may be utilized, and other changes may be made, without departing from the spirit or scope of the subject matter presented here.

The technology is described herein using several definitions, as set forth throughout the specification.

The use of the terms "a" and "an" and "the" and similar referents in the context of describing the elements (especially in the context of the following claims) are to be construed to cover both the singular and the plural, unless otherwise indicated herein or clearly contradicted by context.

As used herein, the term "consisting essentially of" is not an equivalent to the term "comprising." For example, compositions consisting essentially of "food grade agents" are meant to exclude agents that are not "food grade."

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As used herein, the term "substantially reduce" can mean a reduction of greater than 1%, 5%, 10%, 20%, or a value between any two of these percentages.

In certain embodiments, methods are provided of cleaning, disinfecting, or sanitizing without an effluent.

As used herein, the terms "effluent neutral" or "effluent-free" refer to an effluent consisting essentially of water, that need not be chemically or biologically treated (e.g., sanitized, oxidized, neutralized, etc.) before being safely discharged into the environment and/or disposed of in a landfill. Rather, the soiled cleaning, sanitizing, or disinfecting compositions described herein can be concentrated (e.g., by filtration or evaporation) to separate the concentrated composition and/or solids from an effluent consisting essentially of water. In some embodiments, the effluent consisting essentially of water includes one or more salts. In some embodiments, the concentration of salt in the effluent generally ranges from about 0.001 wt % to about 0.01 wt %, about 0.05 wt %, about 0.1 wt %, about 0.5 wt %, about 1 wt %, about 2 wt %, about 3 wt %, about 4 wt %, about 5 wt %, about 6 wt %, about 7 wt %, about 8 wt %, about 9 wt %, about 10 wt %, about 15 wt %, about 20 wt %, about 30 wt %, about 40 wt %, about 50 wt %, or a range between and including any two of these values. In some embodiments, the effluent consisting essentially of water includes a residual concentration of one or more residual food grade agents, as described herein. In some embodiments, the residual concentration of one or more food grade agents in the effluent generally ranges from about 0.001 wt % to about 0.01 wt %, about 0.05 wt %, about 0.1 wt %, about 0.5 wt %, about 1 wt %, about 2 wt %, about 3 wt %, about 4 wt %, about 5 wt %, about 6 wt %, about 7 wt %, about 8 wt %, about 9 wt %, about 10 wt %, about 15 wt %, about 20 wt %, about 30 wt %, about 40 wt %, about 50 wt %, or a range between and including any two of these values.

As used herein, the term "cleaner," "cleaning composition," or "cleaning agent" refers to a composition or agent that, when added to a soiled substrate (e.g., industrial equipment), reduces the amount of soil on the substrate. In certain embodiments, the "cleaner," "cleaning composition," or "cleaning agent" reduces the amount of soil on the soiled substrate (i.e., cleans the substrate) by about 10%, about 20%, about 30%, about 40%, about 50%, about 60%, about 70%, about 80%, about 90%, about 95%, about 99%, or about 100%. The extent to which the "cleaner," "cleaning composition," or "cleaning agent" reduces the amount of soil on the soiled substrate can be measured, for example, according to the procedure of Example 1 or by any procedure known to one of ordinary skill in the art.

As used herein, the term "soil" refers to any foreign substance that is in contact with the substrate, other than the substrate itself. In some embodiments, the soil on the soiled substrate includes a residue of a grain, dairy product, alcoholic beverage, non-alcoholic beverage, fruit, vegetable, meat, animal food, soiled dish residue, an industrial fermentation product, algae, biofuel, pharmaceutical, nutritional supplement, cosmetic or a combination of any two or more thereof.

As used herein, the term "disinfectant," "disinfecting composition," or "disinfecting agent" refers, for example, to a composition or agent that completely destroys all specific test organisms in 10 minutes using the procedure described by the Association of Official Analytical Chemists (A.O.A.C.), "Use Dilution Methods," Official Methods of Analysis of the A.O.A.C., paragraph 955.14 and applicable sections, 15th Edition, 1990 (EPA Guidelines 91-2). Alternatively, the term "disinfectant," "disinfecting composition," or "disinfecting agent" refers to methods defined by CEN 216TC (European Committee for Standardization of disinfectant testing). In certain embodiments, the organisms are pathogenic microorganisms, including fungi, molds, bacteria, spores, and viruses, such as Streptococci, *Legionella, Pseudomonas*, mycobacteria, tuberculosis, phages, or the like. The compositions and agents described herein have activity against a wide variety of microorganisms such as Gram positive (for example, *Listeria monocytogenes* or *Staphylococcus aureus*) and Gram negative (for example, *Escherichia coli* or *Pseudomonas aeruginosa*) bacteria, yeast, molds, bacterial spores, viruses, etc.

As used herein, the term "sanitizer," "sanitizing composition," or "sanitizing agent" refers to an agent that destroys at least 99.999% (5-log reduction) of specified test bacteria within 30 seconds under conditions of the Official Detergent Sanitizer Test (sometimes called the Weber & Black Test). In certain embodiments, a sanitizer reduces the number of bacterial contaminants to safe levels as judged by public health requirements. These reductions can be evaluated using a procedure set out in Germicidal and Detergent Sanitizing Action of Disinfectants, Official Methods of Analysis of the Association of Official Analytical Chemists, paragraph 960.09 and applicable sections, 15th Edition, 1990 (EPA Guidelines 91-2). According to this reference a sanitizer should provide a 99.999% reduction in bacterial contaminants within 30 seconds at 25° C., against test organisms.

As used herein, the term "industrial fermentation" generally refers to the use of microorganisms, including their metabolites or enzymes, to produce commercial products. In some embodiments, industrial fermentation is used to produce foods such as bread, wine, cheese, and curds. In some embodiments, industrial fermentation is used to produce algae, microbial cells or biomass as the product, e.g., bakers yeast, *Lactobacillus, Escherichia coli*, etc. In some embodiments, industrial fermentation is used to produce products that are transformed by microbial enzymes such as catalase, amylase, protease, pectinase, glucose isomerase, cellulase, hemicellulase, lipase, lactase, and streptokinase, etc. In some embodiments, industrial fermentation can be used to produce metabolites such as ethanol, biofuel, citric acid, glutamic acid, lysine, vitamins, and polysaccharides etc.

As used herein, the term "biofuel" refers to any type of fuel derived from biological carbon fixation as opposed to petroleum products such as crude oil. Biofuels include fuels derived from biomass conversion, as well as solid biomass, liquid fuels and various biogases. Biofuels include biodiesel, biogas, and syngas and biologically produced alcohols, such as ethanol or butanol.

Ethanol can be made from renewable resources, primarily by fermentation of carbohydrates produced in sugar or starch crops such as corn or sugarcane. Cellulosic biomass, derived from non-food sources such as trees and grasses, is also a feedstock for ethanol production.

Biodiesel is a diesel additive or replacement for petroleum-based diesel fuel. Biodiesel is made from vegetable oils and/or animal fats. Although biodiesel can be used alone as a fuel for vehicles, it is usually used as a diesel additive to reduce levels of particulates, carbon monoxide, and hydrocarbons from diesel-powered vehicles. It is produced from the fatty acids and esters in oils or fats by transesterification and is a liquid similar in composition to fossil/mineral diesel. Chemically, it consists largely of fatty acid methyl (or ethyl) esters (FAMEs). However, the fatty acids may also be deoxygenated and/or hydrogenated or isomerized to produce biodiesel that even more closely resembles petroleum-based diesel. Feedstocks for biodiesel include animal fats, vegetable oils, soy, rapeseed, jatropha, mahua, mustard, flax, sunflower, palm oil, hemp, field pennycress, pongamia pinnata and algae.

Biogas is methane produced by the process of anaerobic digestion of organic material by anaerobes. It can be produced either from biodegradable waste materials or by the use of energy crops fed into anaerobic digesters to supplement gas yields. The solid byproduct, digestate, can be used as a biofuel or a fertilizer.

Syngas, a mixture of carbon monoxide, hydrogen and other hydrocarbons is produced by partial combustion of biomass, that is, combustion with an amount of oxygen that is not sufficient to convert the biomass completely to carbon dioxide and water. Before partial combustion the biomass is dried, and sometimes pyrolyzed.

As used herein, the terms "triphosphate" and "tripolyphosphate" are used interchangeably.

The present technology provides compositions and methods of cleaning, disinfecting, and sanitizing industrial equipment that are effluent neutral. Such effluent neutral compositions and methods yield an effluent, if any, that consists essentially of water and minimally impacts the environment. As noted, such neutral effluent methods may also recycle the effluent, if any, for one or more additional rounds of cleaning, disinfecting, and sanitizing. The aqueous compositions described herein are added to a soiled piece of equipment and used to clean and dislodge the soiled residues from the equipment. Once the equipment has been cleaned, and thus most of the soiled residues have dissolved or become suspended in the composition, the soiled composition is recovered from the equipment. Upon concentration, water from the recovered composition is optionally recycled and the resulting concentrate and/or soiled solids can be added to animal feed stocks for consumption. The agents and compositions are generally prepared from food grade ingredients and will ultimately be added to animal feed stocks in addition to the soiled residues that have been washed away from industrial equipment.

Cleaning, disinfecting and/or sanitizing treatments of industrial equipment are necessary to reduce microbial populations to safe levels that, in some instances, are established by ordinance or public health regulations. In some embodiments, the method is a method of cleaning. In some embodiments, the method is a method of sanitizing. In some embodiments, the method is a method of disinfecting.

The antimicrobial efficacy of a disinfecting and/or sanitizing treatment is potentially reduced if the surface is not substantially free of soil and other contaminants prior to the disinfecting and/or sanitizing step. The presence of soiling residuals inhibits disinfecting and/or sanitizing treatments by acting as physical barriers which shield microorganisms lying within the organic or inorganic layer from the disinfecting and/or sanitizing composition. Thus, in certain embodiments, a cleaning step is followed by a water rinse and a subsequent disinfecting and/or sanitizing step.

According to one aspect, the present technology provides a method of cleaning, sanitizing, or disinfecting, wherein the method comprises: contacting a soiled substrate with a cleaning, sanitizing, or disinfecting composition, such that at least a portion of the soil is removed from the substrate; wherein the cleaning, sanitizing, or disinfecting composition consists essentially of one or more food grade agents or a salt thereof; and wherein the method is effluent neutral. In some embodiments, methods are provided comprising the removal of a soiled cleaning, sanitizing, or disinfecting composition from the substrate (e.g., industrial equipment) which has been cleaned, sanitized, or disinfected. The method further comprises adding the soiled cleaning, sanitizing, or disinfecting composition to an animal feedstock. In some embodiments, the soiled cleaning, sanitizing, or disinfecting composition is concentrated before being added to an animal feedstock. In some embodiments, the cleaning, sanitizing, or disinfecting composition is substantially dehydrated before being added to the animal feedstock. In some embodiments, the animal is a domestic pet or an animal for food production. In some embodiments, the animal is selected from the group consisting of a sheep, goat, duck, hog, cattle, horse, chicken, dog, cat, and fish.

In some embodiments of the method, the cleaning, sanitizing, or disinfecting composition is combined with a microorganism at a biogas plant for the production of biogas. In further embodiments of the method, the cleaning, sanitizing, or disinfecting composition is added to a fertilizer composition after it has been combined with microorganism at a biogas plant and subsequently recovered following biogas production.

According to another aspect, the present technology provides a method of cleaning, sanitizing, or disinfecting, wherein the method comprises: contacting a soiled substrate with a cleaning, sanitizing, or disinfecting composition, such that at least a portion of the soil is removed from the substrate; where the cleaning, sanitizing, or disinfecting composition consists essentially of one or more (e.g., one, two or three) agents, or a salt thereof, selected from the group consisting of hydroxide, carbonate, bicarbonate, silicate ($SiO_4^{4-}$), monoethanolamine, an enzyme, peroxy acid, hydrogen peroxide, an ethoxylated alcohol, an alkylpolyglycoside, ethyleneoxide/propylene oxide copolymer, octenylsuccinic anhydride, octenylsuccinic acid, aminotrimethylene phosphonic acid, phosphono-1,2,4-butanetricaboxylic acid, gluconic acid, a maleic acid/olefin-copolymer, polyacrylic acid, ethylene diamine tetraacetic acid (EDTA), glutamic acid diacetic acid (GLDA), methyl glycine diacetic acid (MGDA), nitrilo triacetic acid (NTA), caprylic acid, sorbic acid, alkyl ($C_{8-24}$) dibasic fatty acid, alkyl $C_{8-10}$ polyglycolic acid, glycolic acid, citric acid, lactic acid, phosphoric acid, tripolyphosphoric acid, hexametaphosphoric acid, nitric acid, sulphuric acid, methane sulphonic acid, polyalkylene glycol, lauryl dimethyl betaine, and a polydimethyl siloxane emulsion; and where the method is effluent neutral. In some embodiments, the composition consists or consists essentially of just one, two or three of the aforementioned agents.

As noted, in some embodiments, methods of cleaning, sanitizing, or disinfecting are provided, where the methods comprise compositions that consists of or consist essentially of one or more agents. In certain embodiments, the agent is a food grade agent. In certain embodiments, the food grade agent is a sequestrant (e.g., phosphonate, gluconate, polyacrylate), complexing agent, builder, surfactant (e.g., non-ionic surfactant, fatty acid type surfactant, modified fatty acid surfactant, polysorbate, amphoteric surfactant, polysaccharide surfactant, silicone emulsion, or a hydrotrope), an acid, an alkaline additive, or an enzyme.

As used herein, the term "food grade" refers to an agent or substance that can be added to food or a feedstock intended for animal consumption. In certain embodiments, "food grade" refers to an agent or substance considered to be "food grade" by the Food Chemicals Codex (FCC). In certain embodiments, "food grade" refers to an agent or substance classified by the United States Food and Drug Administration (US FDA) as generally regarded as safe (GRAS) and/or classified as food additive, and/or allowed for use on food products and food contact surfaces as those terms are defined by the United States Food and Drug Administration in the Code of Federal Regulations, Chapter 21, Parts 178, 184, and 186. In other embodiments, "food grade" refers to an agent or substance that is GRAS-compliant (i.e., the agent or substance is not registered but would qualify for registration as a food grade additive). In further embodiments, "food grade" refers to an agent or substance that is a "feed material" or "food additive" as these terms are defined by the European Union. Food materials are defined, for example, by Regulations (EC) Nos 1831/2003, 767/2009, and 575/2011 of the European Parliament and of the Council. Food additives are defined, for example, by European Parliament and Council Directive 95/26 EC. As such, each of these agents or substances can be added directly to food or a feedstock, or used in food contact applications. Accordingly, their use is safe for animal consumption and safe in food contact applications.

In some embodiments, the one or more agents, or a salt thereof, is selected from the group consisting of a sequestrant, phosphonate, gluconate, and a polyacrylate. In certain embodiments, the active is a sequestrant. Non-limiting examples of a sequestrant include a phosphonate, a gluconate, and a polyacrylate. Non-limiting examples of a phosphonate include Cublen AP5; Briquest 301-50A; (i.e., aminotrimethylene phosphonic acid 50%); and Cublen P50, Bayhibit AM (i.e., phosphono 1,2,4, butanetricaboxylicacid 50%), and 2-phosphono-butane tricarboxylic acid-1,2,4, polyacrylic acids (e.g., Acusol 445). Non-limiting examples of a gluconate include 50% sodium gluconate. Non-limiting examples of a polyacrylate include Sokalan CP9 (i.e., maleic acid/olefin-copolymer Na-salt, aqueous solution ca. 25%). The concentration of the one or more agents or a salt thereof useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, or a range between and including any two of these values.

In certain embodiments, the one or more agents, or a salt thereof, comprise a complexing agent. Non-limiting examples of a complexing agent include ethylene diamine tetraacetic acid (EDTA, e.g., Trilon BX Na salt, 40%), methyl glycine diacetic acid (MGDA, e.g., Trilon M 3 Na salt 40%), glutamic acid diacetic acid (GLDA, Dissolvine GL38, tetra sodium salt 38%), and nitrilo triacetic acid (NTA, Trilon A 3Na salt, 40%). Nhydroxyethylaminodiacetic acid; hydroxyethylenediaminetetraacetic acid; N-hydroxyethylethylenediaminetriacetic acid (HEDTA); diethylenetriaminepentaacetic acid (DTPA); alanine-N,N-diacetic acid; n-hydroxyethyliminodiacetic acid; and the like. The concentration of complexing agent useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, or a range between and including any two of these values.

In certain embodiments, the one or more agents, or a salt thereof, comprise a builder. Non-limiting examples of a builder include phosphate, tripolyphosphate, a hexametaphosphate, phyllosilicate, and a polyacrylate. In some embodiments, the builder is phosphate. In some embodiments, the builder is tripolyphosphate. In some embodiments, the builder is hexametaphosphate. Non-limiting examples of a phosphate include disodium phosphate (e.g., 100%) and ammonium pyrophosphate. Non-limiting examples of a tripolyphosphate include sodium triphosphate (NaTP, e.g., 50% Polypray H) and potassium triphosphate (KTP, e.g., 50% Solupray P5350). Non-limiting examples of a hexametaphosphate include sodium hexametaphosphate (e.g., 100%) and sodium polymetaphosphate. Non-limiting examples of a polyacrylate include Sokalan CP9 (i.e., maleic acid/olefin-copolymer Na-salt, aqueous solution ca. 25%). The concentration of builder useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, about 60 wt %, about 70 wt %, about 80 wt %, or a range between and including any two of these values.

Additional detergency can be obtained from the use of surfactant materials. The term "surfactant" or "surface active agent" refers to an organic chemical that when added to a liquid changes the properties of that liquid at a surface. In certain embodiments the one or more agents, or a salt thereof, comprise a surfactant. Non-limiting examples of a surfactant include a nonionic surfactant, anionic surfactant, cationic surfactant, fatty acid type surfactant, modified fatty acid surfactant, non-ionic surfactant, polysorbate, amphoteric surfactant, polysaccharide surfactant, silicone emulsion, or a hydrotrope. The concentration of surfactant useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, or a range between and including any two of these values.

The term "non-ionic surfactant," as used herein, typically refers to a surfactant having a hydrophobic group and at least one hydrophilic group comprising a (EO)x group or a (PO)y group wherein x and y are numbers that can range from about 1 to about 100. Non-limiting examples of suitable types of non-ionic surfactant include the ethoxylates of alkyl polyethylene glycol ethers, polyalkylene glycol (e.g., 100% Breox FCC92) and alcohol alkoxylate EO/PO (e.g., Plurafac LF403). Exemplary alcohol ethoxylates include fatty alcohol ethoxylates, e.g., tridecyl alcohol alkoxylate, ethylene oxide adduct, alkyl phenol ethoxylates, and ethoxy/propoxy block surfactants.

Further non-limiting examples of a surfactant include a fatty acid type surfactant such as caprylic acid (e.g., 100% Prifrac 2912). Non-limiting examples of a modified fatty acid include, e.g., alkyl (C21) dibasic fatty acid, Na salt (40%, Diacid H240). The surfactant moiety typically makes up from about 0.01 to about 20.0%, from about 0.05 to about 5.0%, or from about 0.1 to about 2.5% by weight of the cleaning concentrated form of the composition. Non-limiting examples of a polysorbate include potassium sorbate (e.g., Tween 20/60/80). Non-limiting examples of an amphoteric surfactant include lauryl dimethyl betaine (e.g., Empigen BB). Non-limiting examples of a polysaccharide surfactant include alkyl C8-C10 polyglycoside (e.g., 70% Triton BG10). Non-limiting examples of a silicone emulsion include a polydimethyl siloxane emulsion (e.g., Dow Corning Antifoam 1510).

In certain embodiments, the one or more agents, or a salt thereof, comprise a hydrotrope. A hydrotrope is a compound that dissolves hydrophobic compounds in aqueous solutions. Typically, hydrotropes consist of a hydrophilic part and a hydrophobic part (similar to surfactants) but the hydrophobic part is generally too small to cause spontaneous selfaggregation. Exemplary hydrotropes include, inter alia, benzene sulfonates, naphthalene sulfonates, alkyl benzene sulfonates, naphthalene sulfonates, alkyl sulfonates, alkyl sulfates, alkyl diphenyloxide disulfonates, and phosphate ester hydrotropes. Exemplary alkyl benzene sulfonates include, for example, isopropylbenzene sulfonates, xylene sulfonates, toluene sulfonates, cumene sulfonates, as well as mixtures any two or more thereof. Exemplary alkyl sulfonates include hexyl sulfonates, octyl sulfonates, and hexyl/octyl sulfonates, and mixtures of any two or more thereof. The concentration of hydrotrope useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, or a range between and including any two of these values.

In certain embodiments, the one or more agents, or a salt thereof, comprise an acid. Non-limiting examples of an acid include organic and inorganic acids such as glycolic acid (e.g., 70%), citric acid (e.g., 91%), lactic acid (e.g., 80-88%), phosphoric acid (e.g., 75%), nitric acid (e.g., 53%), sulphuric acid (e.g., 75%), methane sulphonic acid (e.g., 70%). The concentration of acid useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, or a range between and including any two of these values.

In certain embodiments, the one or more agents, or a salt thereof, comprise an alkaline additive. Soil removal is commonly achieved using alkaline cleaning compositions. The alkaline additive can be organic, inorganic, and mixtures thereof. Organic sources of alkalinity are often strong nitrogen bases including, for example, ammonia (ammonium hydroxide), amines, alkanolamines, and amino alcohols. In certain embodiments, the one or more agents, or a salt thereof, comprise an alkaline additive. Non-limiting examples of an alkaline additive include caustic soda (NaOH 50%), caustic potash (KOH 50%), lithium hydroxide, silicates (e.g., Pyramid K66, potassium trisilicate solution 33.5-35.5%), ammonia, monoethanolamine (e.g., 99%). Regarding the amount of alkaline additive used in the cleaning composition (if it is desired), typically from about 1.0 to about 20.0%, or from about 2.0 to about 15.0%, or from about 5.0 to about 12.0% by weight of the alkaline additive is employed, based on total weight of the cleaning composition. The concentration of alkaline additive useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, about 60 wt %, or a range between and including any two of these values.

In some embodiments, the one or more agents comprise an enzyme such as a soil-decomposing enzyme. Such enzymes (e.g., cellulases) can be used, for example, to clean surfaces and degrade fibrous cellulose residuals. Further, non-limiting examples of an enzyme, include but are not limited to hemicellulases, peroxidases, proteases, cellulases, xylanases, lipases, phospholipases, esterases, cutinases, pectinases, pectate lyases, amylases, mannanases, keratinases, reductases, oxidases, phenoloxidases, lipoxygenases, ligninases, pullulanases, tannases, pentosanases, malanases, beta-glucanases, arabinosidases, hyaluronidase, chondroitinase, laccase, and amylases, or mixtures of any two or more thereof. In some embodiments, a combination of enzymes (i.e., an "enzyme cocktail") comprising conventional applicable enzymes like a protease, lipase, amylase, pectinase, cutinase and/or cellulase. The concentration of enzyme useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, or a range between and including any two of these values.

In some embodiments, the one or more agents are food grade agents. In some embodiments, the one or more agents, or a salt thereof, is a food grade agent selected from the group consisting of hydroxide, carbonate, bicarbonate, silicate ($SiO_4^{4-}$), monoethanolamine, an enzyme, peroxy acid, hydrogen peroxide, an ethoxylated alcohol, an alkylpolyglycoside, ethyleneoxide/propylene oxide copolymer, octenylsuccinic anhydride, octenylsuccinic acid, aminotrimethylene phosphonic acid, phosphono-1,2,4-butanetricaboxylic acid, gluconic acid, a maleic acid/olefin-copolymer, polyacrylic acid, ethylene diamine tetraacetic acid (EDTA), glutamic acid diacetic acid (GLDA), methyl glycine diacetic acid (MGDA), nitrilo triacetic acid (NTA), caprylic acid, sorbic acid, alkyl ($C_{8-24}$) dibasic fatty acid, alkyl $C_{8-10}$ polyglycolic acid, glycolic acid, citric acid, lactic acid, phosphoric acid, tripolyphosphoric acid, hexametaphosphoric acid, nitric acid, sulphuric acid, methane sulphonic acid, polyalkylene glycol, lauryl dimethyl betaine, and a polydimethyl siloxane emulsion. In some embodiments, the cleaning composition consists of or consists essentially of one, two, three or four of the foregoing agents. In some embodiments, the one or more food grade agents are GRAS Certified. In some embodiments, the one or more agents comprise fertilizer agents. In some embodiments, the one or more food grade agents are GRAS compliant (i.e., the agent or substance is not registered but would qualify for registration as a food grade additive). In some embodiments, at least one of the one or more food grade agents is an acid. In some embodiments, at least one of the one or more food grade agents is an acid having a pKa in water of less than 6.0. In some embodiments, at least one of the one or more food grade agents is an acid having a pKa in water of less than 4.0. The concentration of food grade agents useful in some embodiments generally ranges from about 0.01 wt % to about 0.1 wt %, about 1 wt %, about 2 wt %, about 3 wt %, about 4 wt %, about 5 wt %, about 10 wt %, about 20 wt %, about 30 wt %, about 40 wt %, about 50 wt %, about 60 wt %, about 70 wt %, about 80 wt %, about 90 wt %, about 100 wt %, or a range between and including any two of these values.

In some embodiments, the one or more agents are compliant with biogas plants. In other words, cleaning compositions comprising the one or more agents can be used to clean production equipment within a biogas plant without hindering biogas production. In some embodiments, methods are provided of cleaning, sanitizing, or disinfecting a brewery, or portions thereof, where the methods comprise compositions that consist essentially of one or more agents described herein. After the brewery, or portions thereof, has been cleaned, sanitized, or disinfected, the soiled cleaning residues, having traces of the one or more agents described herein are collected. In some embodiments, the soiled cleaning residues are used as a feedstock for microorganisms, at a biogas production plant. The microorganisms metabolize at least some of this soiled cleaning feedstock into biogas. The remaining cleaning residue feedstock that is not converted into biogas can be collected, combined with fertilizers, and used as a fertilizer composition.

In some embodiments, the one or more agents or a salt thereof is selected from the group consisting of tripolyphosphoric acid, hydroxide, carbonate, hydrogen peroxide and peracetic acid. In some embodiments, the cleaning, sanitizing, or disinfecting composition consists of about 0.01-5.0 wt. % potassium tripolyphosphoric acid, 0-5.0 wt. % sodium hydroxide, 0-2.0 wt. % sodium carbonate, 0-2.0 wt. % hydrogen peroxide, 0-2.0 wt. % peracetic acid and water. In some embodiments, the composition has a pH of about 7.0 to about 14.0.

In some embodiments, the one or more food grade agents are selected from hydroxide, carbonate, bicarbonate, and silicate ($SiO_4^{4-}$).

In some embodiments, the one or more food grade agents are selected from monoethanolamine, an enzyme, peroxy acid, (e.g., peracetic acid) and hydrogen peroxide.

In some embodiments, the one or more food grade agents are selected from an ethoxylated alcohol, an alkylpolyglycoside, ethyleneoxide/propylene oxide copolymer, octenylsuccinic anhydride, and octenylsuccinic acid.

In some embodiments, the one or more food grade agents are selected from aminotrimethylene phosphonic acid, phosphono-1,2,4-butanetricaboxylic acid, gluconic acid, a and maleic acid/olefin-copolymer.

In some embodiments, the one or more food grade agents are selected from polyacrylic acid, ethylene diamine tetraacetic acid (EDTA), glutamic acid diacetic acid (GLDA), methyl and glycine diacetic acid (MGDA).

In some embodiments, the one or more food grade agents are selected from nitrilo triacetic acid (NTA), caprylic acid, sorbic acid, alkyl ($C_{8-24}$) dibasic fatty acid, alkyl $C_{8-10}$ polyglycolic acid, and glycolic acid.

In some embodiments, the one or more food grade agents are selected from citric acid, lactic acid, phosphoric acid, tripolyphosphoric acid, and hexametaphosphoric acid.

In some embodiments, the one or more food grade agents are selected from nitric acid, sulphuric acid, methane sulphonic acid, polyalkylene glycol, lauryl dimethyl betaine, hydrogen peroxide, and a polydimethyl siloxane emulsion.

In certain embodiments, the cleaning, sanitizing, or disinfecting composition consists essentially of a mixture of phosphoric acid, one or more organic acids, and a hydrotrope agent ("Product 1"). In certain embodiments, the cleaning, sanitizing, or disinfecting composition consists essentially of a mixture of one or more acids and hydrogen peroxide ("Product 2"). Product 1 and Product 2 are described in Example 1 below.

The pH of the cleaning, sanitizing, or disinfecting composition can and will vary. For example, the pH of the cleaning, sanitizing, or disinfecting composition will be from about 0.1 to about 1, about 2, about 3, about 4, about 5, about 6, about 7, about 8, about 9, about 10, about 11, about 12, or a range between and including any two of these values.

The viscosity of the cleaning, sanitizing, or disinfecting composition can and will vary. In certain embodiments, the cleaning, sanitizing, or disinfecting composition has a viscosity from about 1.0 to about 2.0 cps, about 4.0 cps, about 6.0 cps, about 8.0 cps, about 10.0 cps, about 12.0 cps, about 14.0 cps, about 16.0 cps, about 18.0 cps, about 20.0 cps, or a range between and including any two of these values. Such a viscosity is based on viscosity measurements that may be taken with a Brookfield Viscometer, at ambient temperature, and with Spindle No. 1 from the LV set.

When making the cleaning, sanitizing, or disinfecting composition of some embodiments, the one or more agents (e.g., sequestrant, phosphonate, gluconate, polyacrylate, complexing agent, builder, surfactant, an acid, an alkaline additive, or an enzyme) are added to a mixing vessel (in no particular order) and stirred, for example, under conditions of moderate sheer at ambient temperature and atmospheric pressure. In certain embodiments, the agents are food grade agents. The resulting cleaning, sanitizing, or disinfecting concentrate composition may be sold as is and with instructions to dilute with water (to form cleaning, sanitizing, or disinfecting use-solution) prior to use.

In some embodiments, the cleaning, sanitizing, or disinfecting composition is a concentrated composition. In certain embodiments, the concentrated composition is an aqueous solution having a ratio of food grade agents to water of from 3:1 to 1:100. In some embodiments, the water typically makes up from about 5 wt %, about 10 wt %, about 20 wt %, about 30 wt %, about 40 wt %, about 50 wt %, about 60 wt %, about 70 wt %, about 80 wt %, about 90 wt %, about 99 wt %, or a range between and including any two of these values. In certain embodiments, the water typically makes up from about 35.0% to about 70.0%, from about 35.0% to about 55.0%, or from about 35.0% to about 45.0% by weight of the concentrated aqueous solution.

In some embodiments, concentrated solution of the cleaning, sanitizing, or disinfecting composition is combined with diluent (e.g., water) to form a use-solution. Alternatively the use solution can also be produced directly by dissolving the solid block of the concentrated composition with the necessary amount of water. In some embodiments, the use-solution has a ratio of cleaning-composition to water of from about 1:100 to about 1:10000, or from about 1:100 to about 1:2000. In some embodiments, the concentrated compositions can be diluted, for example, with water at a dilution ratio of about 0.1 g/L to about 100 g/L concentrate to diluent, about 0.5 g/L to about 10.0 g/L concentrate to diluent, about 1.0 g/L to about 4.0 g/L concentrate to diluent, or about 1.0 g/L to about 2.0 g/L concentrate to diluent. In other embodiments, a use solution can include about 0.01 to about 10 wt % of a concentrate composition and about 90 to about 99.99 wt % diluent; or about 0.1 to about 1 wt % of a concentrate composition and about 99 to about 99.9 wt % diluent. Such use-solutions can be applied to a variety of industrial equipment for removal of a variety of soil types, disinfection, and/or sanitization. They are useful for application in clean-in-place (CIP) and sanitize-in-place (SIP) systems within food and beverage processing facilities.

In some embodiments, the diluted use-solution is applied to soiled industrial equipment to clean, sanitize, or disinfect the industrial equipment. In so doing, the use-solution becomes soiled. In some embodiments, the soiled use-solution can be recovered from the industrial equipment and reused (i.e., optionally recycled) for further cleaning, sanitizing, or disinfecting. Thus, in some embodiments, the method includes recycling the cleaning, sanitizing, or disinfecting composition for further use in cleaning, sanitizing, or disinfecting additional soiled substrates. In some embodiments, the cleaning, sanitizing, or disinfecting composition comprises solids that are separated before the solution is further used in cleaning, sanitizing, or disinfecting soiled substrates. In some embodiments, the separated solids are added to an animal feedstock.

In some embodiments, the method of cleaning, sanitizing, or disinfecting comprises mechanical dish-washing. In some embodiments, the substrate is a dish-washing apparatus (e.g., dishwasher). The dishwasher (e.g., such that used in a restaurant or healthcare facility) is used to clean and sanitize cooking and eating articles, such as, dishes, bowls, cups, glasses, pots, pans, utensils and other cooking or food-serving equipment.

In some embodiments, the method of cleaning, sanitizing, or disinfecting is a clean-in-place (CIP), sanitize-in-place (SIP), a clean-out-of-place (COP), or a sanitize-out-of-place (SOP) method. COP and SOP systems include readily accessible substrates of industrial equipment, including wash tanks, soaking vessels, holding tanks, scrub sinks, vehicle parts washers, noncontinuous batch washers and systems, and the like. CIP and SIP systems include the internal components of industrial equipment such as tanks, lines, pumps and other equipment used for processing typically liquid product streams such as beverages, milk, and juices.

Automated clean-in-place (CIP) and sanitize-in-place (SIP) techniques have reduced the need for industrial equipment disassembly and increased the efficiency of cleaning and sanitizing methods. CIP or SIP techniques use the combination of chemistry and mechanical action to clean the inside of industrial equipment without requiring the time consuming and labor intensive disassembly and manual cleaning of a system. CIP or SIP techniques generally include the circulation of chemistries (e.g., cleaners, sanitizers, or disinfectants and the like) for periodic cleaning of industrial equipment. In some embodiments, CIP or SIP techniques involve a first rinse, the application of cleaning or sanitizing solutions, a second rinse with potable water, followed by resumed operations. In some embodiments, one or both rinses are omitted. The process can also include any other contacting step in which a rinse, acidic or basic functional fluid, solvent or other cleaning component such as hot water, cold water, etc. can be contacted with the equipment at any step during the process.

Industrial equipment (e.g., brewery or dairy equipment) may be cleaned sanitized, or disinfected using CIP or SIP techniques. The cleaning, sanitizing, or disinfecting of the in-place systems is accomplished with the present compositions, and according to the present methods, with heated, ambient, or cooled water. In some embodiments, the concentrated composition is introduced into an in-place system (e.g., industrial equipment) and diluted, in situ, with water. Alternatively, the composition is applied or introduced into the system as a use-solution. CIP or SIP techniques typically employ flow rates of about 0.1 meters per second to about 0.5 meters per second, about 1.0 meter per second, about 1.1 meters per second, about 1.2 meters per second, about 1.3 meters per second, about 1.4 meters per second, about 1.5 meters per second, about 1.6 meters per second, about 1.7 meters per second, about 1.8 meters per second, about 1.9 meters per second, about 2.0 meters per second, about 2.5 meters per second, about 3.0 meters per second, about 3.5 meters per second, about 4.0 meters per second, about 4.5 meters per second, about 5.0 meters per second or a range between and including any two of these values.

CIP or SIP techniques can employ the present cleaning, sanitizing, or disinfecting solution with cold (e.g., 4° C., 10° C., 15° C.), ambient, or heated (e.g., 40° C., 50° C., 60° C., 70° C., 80° C., 85° C., 90° C., 95° C., 100° C.) water. CIP or SIP techniques can employ contact times of at least about 2 seconds, about 5 seconds, about 10 seconds, about 15 seconds, about 20 seconds, about 30 seconds, about 60 seconds, about 90 seconds, about 120 seconds, 5 minutes, 15 minutes, 30 minutes, one hour, two hours, or a range between and including any two of these values.

In some embodiments, methods are provided comprising the removal of a soiled cleaning, sanitizing, or disinfecting composition from the industrial equipment which has been cleaned, sanitized, or disinfected using CIP or SIP techniques. The method further comprises adding the soiled cleaning, sanitizing, or disinfecting composition to an animal feedstock. In some embodiments, the soiled cleaning, sanitizing, or disinfecting composition is concentrated before being added to an animal feedstock. In some embodiments, the cleaning, sanitizing, or disinfecting composition is substantially dehydrated before being added to the animal feedstock.

In some embodiments, the method of cleaning, sanitizing, or disinfecting is carried out under an atmosphere comprising a higher percentage of carbon dioxide than in air. In certain embodiments, the method of cleaning, sanitizing, or disinfecting is carried out under an atmosphere comprising a higher percentage of carbon dioxide, where the method comprises clean-in-place or sanitize-in-place techniques. Alkaline cleaning, disinfecting, or sanitizing compositions are poorly suited to an atmosphere comprising carbon dioxide because residual carbonic acid will react with the alkaline agents to form carbonate. In some embodiments, the cleaning, disinfecting, or sanitizing compositions described herein that have a pH of <7 are used to clean equipment under an atmosphere comprising a higher percentage of carbon dioxide than air. In some embodiments, the cleaning, disinfecting, or sanitizing compositions described herein that have a pH of >7 are used to clean equipment under an atmosphere comprising a higher percentage of carbon dioxide than air. The carbonate formed, if any, in the cleaning, sanitizing, or disinfecting composition does not substantially reduce the efficacy of the composition. For example, in some embodiments, the substrate is a brewing apparatus for an alcoholic beverage. In some embodiments, carbonate is formed in the cleaning, sanitizing, or disinfecting composition, and the carbonate does not substantially reduce activity of an enzyme used during liquification or fermentation of sugar-based materials during the production of an alcohol. In some embodiments, the residual cleaning, sanitizing, or disinfecting composition that remains in the apparatus, after cleaning, contacts the brewed beverage. In some embodiments, the brewed beverage is beer. In some embodiments, the substrate is a fermentation apparatus for the fermentation of a sugar-based material into a biofuel. In some embodiments, the biofuel is selected from the group consisting of ethanol, butanol, biodiesel, biogas and syngas.

According to another aspect, the present technology provides an animal feedstock. The animal feed stock prepared according to the present technology is of sufficient quality that it may be used in any contemporary animal food product. In certain embodiments, the animal feedstock comprises animal feed and a soiled cleaning, sanitizing, or disinfecting composition, wherein the soiled cleaning, sanitizing, or disinfecting composition consists essentially of (i) one or more residues comprising a grain, dairy, alcoholic beverage, non-alcoholic beverage, fruit, vegetable, meat, animal food, soiled dish, industrial fermentation product, algae, biofuel, pharmaceutical, nutritional supplement, cosmetic or a combination of any two or more thereof.

In some embodiments of the animal feedstock, the one or more cleaning, sanitizing, or disinfecting agents is selected from the group consisting essentially of hydroxide, carbonate, bicarbonate, silicate ($SiO_4^{4-}$), monoethanolamine, an enzyme, peroxy acid (e.g., peracetic acid), hydrogen peroxide, an ethoxylated alcohol, an alkylpolyglycoside, ethyleneoxide/propylene oxide copolymer, octenylsuccinic anhydride, octenylsuccinic acid, aminotrimethylene phosphonic acid, phosphono-1,2,4-butanetricaboxylic acid, gluconic acid, a maleic acid/olefin-copolymer, polyacrylic acid, ethylene diamine tetraacetic acid (EDTA), glutamic acid diacetic acid (GLDA), methyl glycine diacetic acid (MGDA), nitrilo triacetic acid (NTA), caprylic acid, sorbic acid, alkyl ($C_{8-24}$) dibasic fatty acid, alkyl $C_{8-10}$ polyglycolic acid, glycolic acid, citric acid, lactic acid, phosphoric acid, tripolyphosphoric acid, hexametaphosphoric acid, nitric acid, sulphuric acid, methane sulphonic acid, salts of any of the foregoing acids, polyalkylene glycol, lauryl dimethyl betaine, hydrogen peroxide, and a polydimethyl siloxane emulsion.

In further embodiments of the animal feedstock, the one or more cleaning, sanitizing, or disinfecting agents is selected from the group consisting essentially of tripolyphosphoric acid, hydroxide, carbonate, hydrogen peroxide and an organic peroxyacid. In some embodiments of the animal feedstock, the one or more agents comprise fertilizer agents. In additional embodiments of the animal feedstock, the one or more agents are compliant with biogas plants.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology, thus generally described, will be understood more readily by reference to the following Examples, which are provided by way of illustration and are not intended to be limiting of the present technology.

EXAMPLES

Example 1

Reference Cleaning Tests and Cleaning Tests Using Compositions for Use in Cleaning Effluent Neutral Methods Cleaning tests with reference cleaners and cleaning compositions for use in effluent neutral methods were carried out according to the same protocol to compare the cleaning effectiveness of each. The results for the reference cleaning tests are provided below in Table 1. The results for cleaning compositions for use in effluent neutral methods are provided in Table 2. A comparative summary of the cleaning effectiveness of reference cleaners and cleaning compositions for use in effluent neutral methods is provided in Table 3.

Soiling Used:
A soiling "ferment" paste consisting of grains, water, yeast and other fermentation by-products were used to soil samples of mild steel. The grains were those typically found in brewing and cereal fermentation.

Method & Results:

Mild steel plates were prepared and cleaned as described below.

Plate Pre-Treatment:

The steel test plates (6"×4"×0.8 mm, i.e., 15.2×10.2 cm×0.8 mm) were degreased by sequentially scrubbing with ShurClean Plus® (Diversey Inc. De Boelelaan 32 HJ 1083 Amsterdam, The Netherlands) and sodium carbonate followed by wiping the surface with a paper towel soaked in acetone.

Plate Soiling:

The cleaned plates were placed on a horizontal surface, the ferment paste (5 grams) was weighed onto the surface and spread using a pallet knife. This was repeated after the plate had dried for 2 hours. Plates were left to dry overnight before use. Each plate was used only once to give a uniform surface for soil adhesion because of corrosion of the mild steel during each test.

Cleaning Procedure:

Plates were suspended in a 2.5 liter tall-form beaker containing 2.2 liters of a test cleaning solution at a 80° C., unless otherwise specified below. Liquid was continuously mixed using a magnetic stirrer during the 30 minute test period.

Measurements:

Test plates were photographed before and after the cleaning procedure. Plates were weighed (1) before cleaning, (2) after cleaning and overnight drying, and (3) after removal of the residual soil. Percent soil removal was calculated from the difference between pre-cleaning and post-cleaning weights divided by the difference between pre-cleaning and post cleaning residual cleaning weights: (removed mass/added mass)×100=% cleaning performance. Tests detergent solutions were prepared at listed strength in distilled water.

Results:

Weight differences at the various stages of the tests upon duplicate plates are shown below in Tables 1 and 2. The relative cleaning effectiveness of the reference cleaners and several representative Effluent Neutral compositions is shown in Table 3.

TABLE 1

Results on mild steel plates of Cleaning Tests Using Reference Cleaners.

| Test Solution | Weight of soiled Panel [g] | Weight of Panel after Test [g] | Weight of cleaned Panel [g] | Weight of soil [g] | Weight of removed soil [g] | Soil Removal [%] |
|---|---|---|---|---|---|---|
| 2% Caustic | 107.76 | 106.58 | 106.36 | 1.4 | 1.18 | 84 |
| Soda | 109.06 | 107.86 | 107.59 | 1.47 | 1.2 | 82 |
| Water | 108.01 | 107.46 | 106.59 | 1.42 | 0.55 | 39 |
|  | 108.83 | 108.22 | 107.4 | 1.43 | 0.61 | 43 |
| 3% Sodium | 107.61 | 106.96 | 106.15 | 1.46 | 0.65 | 45 |
| Carbonate | 108.35 | 107.84 | 106.99 | 1.35 | 0.5 | 37 |
| 5% Carbonate + 4% | 89.54 | 89.14 | 88.3 | 1.24 | 0.4 | 32.3 |
| Bicarbonate | 90.22 | 89.77 | 88.92 | 1.30 | 0.45 | 34.6 |

TABLE 2

Results on mild steel plates of cleaning tests using representative cleaning compositions for use in effluent neutral methods.

| Test Solution | Weight of soiled Panel [g] | Weight of Panel after Test [g] | Weight of cleaned Panel [g] | Weight of soil [g] | Weight of removed soil [g] | Soil Removal [%] |
|---|---|---|---|---|---|---|
| Sequestrants: e,g., Phosphonates, Gluconates, Potyacrylates | | | | | | |
| 0.1% Sodium | 89.93 | 89.40 | 88.72 | 1.21 | 0.53 | 44 |
| Gluconate | 90.53 | 89.99 | 89.52 | 1.01 | 0.54 | 53 |
| pH 5.0 | | | | | | |
| 0.1% Sodium | 90.37 | 90.56 | 89.0 | 1.37 | 0.87 | 64 |
| Gluconate | 90.08 | 90.36 | 88.80 | 1.28 | 0.72 | 56 |
| pH 9.0 | | | | | | |
| 0.1% Sodium | 91.13 | 90.56 | 89.85 | 1.28 | 0.58 | 45 |
| Gluconate | 90.93 | 90.36 | 89.65 | 1.28 | 0..57 | 45 |
| pH 7.0 | | | | | | |
| Complexing agents: e.g., EDTA | | | | | | |
| 0.2% EDTA | 90.12 | 89.34 | 88.82 | 1.30 | 0.78 | 60 |
|  | 90.58 | 89.74 | 89.31 | 1.27 | 0.84 | 66 |
| Builders: e,g., Phosphates (STPP, KTPP) | | | | | | |
| 1% Sodium | 89.70 | 88.67 | 88.43 | 1.27 | 1.03 | 81 |
| Triphosphate | 90.43 | 89.24 | 89.11 | 1.32 | 1.19 | 90 |
| 0.5% KTPP | 82.52 | 81.30 | 81.28 | 1.24 | 1.22 | 98 |
| pH 9.0 | 82.74 | 81.45 | 81.43 | 1.31 | 1.29 | 98 |

TABLE 2-continued

Results on mild steel plates of cleaning tests using representative cleaning compositions for use in effluent neutral methods.

| Test Solution | Weight of soiled Panel [g] | Weight of Panel after Test [g] | Weight of cleaned Panel [g] | Weight of soil [g] | Weight of removed soil [g] | Soil Removal [%] |
|---|---|---|---|---|---|---|
| Surfactants: e.g., Caprylic acid, Non-Ionics, Polysorbates, Silicones | | | | | | |
| 0.1% Caprylic | 90.59 | 90.06 | 89.31 | 1.28 | 0.53 | 41 |
| acid | 90.50 | 89.96 | 89.23 | 1.27 | 0.54 | 43 |
| Product 1: Blend consisting of phosphoric acid, organic acid and hydrotrope | | | | | | |
| 3% Product 1 | 90.54 | 89.33 | 89.32 | 1.22 | 1.21 | 99 |
| at 60° C. | 90.46 | 89.24 | 89.24 | 1.22 | 1.22 | 100 |
| Product 2: Blend consisting of phosphoric acid and hydrogen peroxide | | | | | | |
| 3% Product 2 | 112.91 | 111.74 | 111.73 | 1.18 | 1.17 | 99 |
| at 60° C. | 112.35 | 111.13 | 111.13 | 1.22 | 1.22 | 100 |
| 3% Product 2 | 89.87 | 89.05 | 88.64 | 1.23 | 0.82 | 67 |
| at 40° C. | 90.37 | 98.62 | 89.12 | 1.25 | 0.75 | 60 |

TABLE 3

Comparative Summary on mild steel plates of the Cleaning Test Results

| Test Solution | Soil Removal [%] |
|---|---|
| Reference cleaners | |
| 2% Caustic Soda | 83 |
| Water | 41 |
| 3% Sodium Carbonate | 41 |
| 5% Carbonate + 4% Bicarbonate | 34 |
| "Effluent Neutral" cleaners | |
| 0.1% Sodium Gluconate pH 5.0 | 49 |
| 0.1% Sodium Gluconate pH 9.0 | 60 |
| 0.1% Sodium Gluconate pH 7.0 | 45 |
| 0.2% EDTA | 63 |
| 1% Sodium Triphosphate | 86 |
| 0.5% KTPP pH 9.0 | 98 |
| 0.1% Caprylic acid | 42 |
| 3% Product 1 at 60° C. | 100 |
| 3% Product 2 at 40° C. | 64 |

The results shown in Tables 1-3 demonstrate that a member of the representative cleaning compositions for use in effluent neutral methods were extremely effective. Some of these compositions more effectively cleaned soil (e.g., ferment paste) from mild steel than conventional cleaners. For example, compositions having 1% sodium triphosphate and 0.5% KTPP at pH 9.0 were effective cleaners. Products 1 and 2 were also effective, particularly at lower temperatures (e.g., 40° C., 60° C.).

Conclusions:

The cleaning, sanitizing, or disinfecting compositions described herein are comparable or superior to the conventional compositions that were tested. Further, the cleaning, disinfecting, and sanitizing compositions, as described herein, can be used to clean industrial equipment without generating an effluent stream. Rather, once the industrial equipment has been cleaned, and thus most of the soiled residues have dissolved or become suspended in the composition, the soiled composition is recovered from the equipment. Upon concentration, water from the recovered composition is optionally recycled and the resulting concentrate and/or soiled solids can be added to animal feed stocks for consumption. Such compositions and methods of cleaning, disinfecting, and sanitizing industrial equipment minimally impact the environment by reducing or eliminating the effluent discharge of spent cleaning solutions, recycling the water supply, and converting an industrial waste stream into an animal feed stock.

Example 2

Cleaning Formulations

The cleaning formulations shown below in Table 4 were prepared and tested.

TABLE 4

Cleaning Formulations.

| Cleaning Formulation | Ingredients | % (w/w) |
|---|---|---|
| A | ethylene diamine tetraacetic acid 4Na-salt | 40 |
| B | Mixture of polyphosphates $P_2O_5 > 20\%$ | 50 |
| C | gluconic acid Na-salt | 33 |
|  | sodium hydroxide | 3 |
|  | aminotrimethylene phosphonic acid | 2 |
| D | cumene sulphonic acid Na-salt | 8 |
|  | phosphoric acid | 26 |
|  | glycolic acid | 5 |
|  | fatty (caprylic) acid | 1 |
|  | n-octenyl succinic anhydride | 3 |
| E | Acetic Acid | 18-22 |
|  | Peracetic Acid | 15 |
|  | Hydrogen Peroxide | 23 |
|  | Stabilizers | <2 |

Example 3

Cleaning Tests at 70° C.

Inorganic deposits (e.g., scale) may form in equipment such as fermentation tanks during cleaning with caustic soda under a $CO_2$ atmosphere. This formation of hardness scale may result in reduced cleaning action, reduced heat efficiency and galvanic corrosion. Various cleaning compositions were evaluated that compared various proportions of caustic soda and/or $Na_2CO_3$ against compositions that lacked these components. Temperatures were maintained at 70° C. Cleaning time was 45 min.

Preparation of Steel Plates with Bioferment:

Stainless steel plates soiled with a thin layer of ferment coming from a biofermentation plant were dried over night at ambient temperature.

Cleaning Tests:

The soiled plates were submerged in a beaker containing one of the reference or test cleaning solutions. Low mechanical impact was maintained with magnetic stirring. Test panels were photographed before and after the cleaning procedure. Plates were weighed before cleaning, after drying overnight post cleaning procedure and after cleaning and drying to remove residual soil.

Results:

The results are shown below in Table 5.

caustic with carbon dioxide. Moreover, compositions having formulation B can improve work place safety because they are less hazardous than formulations containing high concentrations of caustic soda.

Cleaning Formulation C:

Compositions having Formulation C deliver good cleaning results but are generally designed to be additives to alkaline liquid detergents, primarily to provide sequestration in caustic solutions and to prevent scale formation in CIP applications and spray washing applications. Compositions having Formulation C are generally not intended for use without caustic soda as a single phase cleaner.

2% NaOH, 1% NaOH+1% Soda ($Na_2CO_3$) and 2% Soda:

Without further additives, that basic composition demonstrated the least effective cleaning results.

TABLE 5

Comparative Cleaning Results at 70° C. (45 min contact time).

| # | | Steel Plate AISI 304 | Soiled Steel Plate [g] | Weight Soils Before Clean [g] | Cleaned Steel Plate [g] | Weight Soils After Clean [g] | Soil Removal [g] | Soil Removal Average [g] |
|---|---|---|---|---|---|---|---|---|
| 1 | 2% NaOH | 39.4452 | 39.6418 | 0.1966 | 39.4479 | 0.0027 | 98.6 | 98.46 |
| 2 | | 39.3718 | 39.6478 | 0.276 | 39.3765 | 0.0047 | 98.3 | |
| 3 | 1% NaOH + 1% | 39.5321 | 39.8002 | 0.2681 | 39.5361 | 0.004 | 98.5 | 98.13 |
| 4 | $Na_2CO_3$ | 39.554 | 39.7455 | 0.1915 | 39.5583 | 0.0043 | 97.8 | |
| 5 | 2% $Na_2CO_3$ | 39.5597 | 39.8021 | 0.2424 | 39.5742 | 0.045 | 94.0 | 92.29 |
| 6 | | 39.5808 | 39.838 | 0.2572 | 39.6051 | 0.0243 | 90.6 | |
| 7 | 1% Formulation B | 39.3485 | 39.838 | 0.2832 | 39.3488 | 0.0243 | 99.6 | 99.93 |
| 8 | | 39.4394 | 39.7673 | 0.3279 | 39.4395 | 0.0001 | 100.0 | |
| 9 | 2% NaOH + | 39.4353 | 39.6746 | 0.2393 | 39.437 | 0.0017 | 99.3 | 99.5 |
| 10 | 2% Formulation B | 39.2569 | 39.4941 | 0.2372 | 39.2577 | 0.0008 | 99.7 | |
| 11 | 1% NaOH + | 39.3406 | 39.577 | 0.2364 | 39.3433 | 0.0027 | 98.9 | 98.7 |
| 12 | 1% $Na_2CO_3$ + 0.2% Formulation B | 39.4386 | 39.691 | 0.2524 | 39.4421 | 0.0035 | 98.6 | |
| 13 | 2% NaOH + 0.2% | 39.5171 | 39.7602 | 0.2431 | 39.5202 | 39.5171 | 98.7 | 98.3 |
| 14 | Formulation A | 39.3986 | 39.7415 | 0.3429 | 39.4057 | 39.3986 | 97.9 | |
| 15 | 1% NaOH + | 39.3818 | 39.6472 | 0.2654 | 39.3843 | 39.3818 | 99.1 | 98.3 |
| 16 | 1% $Na_2CO_3$ + 0.2% Formulation A | 39.4551 | 39.7038 | 0.2487 | 39.4611 | 39.4551 | 97.6 | |
| 17 | 2% NaOH + 0.2% | 39.2503 | 39.5295 | 0.2792 | 39.2517 | 39.2503 | 99.5 | 99.5 |
| 18 | Formulation C | 39.4838 | 39.7834 | 0.2996 | 39.4855 | 39.4838 | 99.4 | |
| 19 | 1% NaOH + | 39.6896 | 39.9096 | 0.22 | 39.6911 | 39.6896 | 99.3 | 99.2 |
| 20 | 1% $Na_2CO_3$ + 0.2% Formulation C | 39.5395 | 39.8041 | 0.2646 | 39.5418 | 39.5395 | 99.1 | |

Cleaning Formulation B:

Compositions having Formulation B provide improved cleaning performance and water hardness stabilization. These compositions also provide impressive visual results based on the appearance of the cleaned plates by showing reduced soil redeposition against control panels. Compositions having Formulation B are capable as additives to caustic, as water hardness sequestrants and as single phase cleaners. Compositions having Formulation B are approximately neutral in a $CO_2$ atmosphere and generally comply with requirements regarding residues in dried distiller's grains with solubles (DDGS). Using Formulation B as single cleaner substantially prevents soda ($Na_2CO_3$) formation and scale formation. Reduced scale formation reduces maintenance costs (e.g., replacement of valves or processing equipment like spray heads or pressure gauges). In addition, compositions having formulation B can increase or improve cleaning performance of caustic when level of soda and/or bicarbonate levels start to increase due to the reaction of Example 4

Cleaning Tests at Various Temperatures

Methods:

Stainless steel plates were prepared and cleaned using a modified procedure according to current practice F&B 024.

Plate Pre-Treatment:

Stainless steel test plates (6"×4"×0.8 mm) were degreased by sequentially scrubbing with ShurClean Plus® (Diversey Inc. De Boelelaan 32 HJ 1083 Amsterdam, The Netherlands) and sodium carbonate followed by wiping the surface with a paper towel soaked in acetone.

Plate Soiling:

Cleaned plates were placed on a horizontal surface, 5 grams of ferment were weighed onto the surface and spread using a pallet knife. This was repeated after the plate had dried for 2 hours. Plates were left to dry overnight before use. It was not possible to carry out a 4×2.5 gram of soil application as specified in CP F&B 024 because of the nature of the solids in the ferment.

Cleaning Procedure:

Plates were suspended in a 2.5 liter tall form beaker containing 2.2 liters of test detergent solution at temperature as specified. Liquid was continuously mixed using a magnetic stirrer during the 30 minute test period. Larger volumes of detergent solution were required than stated in CP F&B 024 because of the size of the test panel and to avoid the mild steel test panel interfering with the magnetic stirrer.

Measurements:

Test panels were photographed before and after the cleaning procedure. Plates were weighed before cleaning, after drying overnight post cleaning procedure and after cleaning and drying to remove residual soil. Percent soil removal was calculated from the difference between pre and post cleaning weights divided by the difference between pre and post residual cleaning weights. Tests detergent solutions were prepared in distilled water.

Results:

As shown in Table 6 (these tests were carried out on mild steel) and FIG. 1 (these tests were carried out on stainless steel), the results indicate that decreasing the cleaning temperature decreases the effectiveness of the tested detergents at removing the fermenting soil. Water, caustic soda and mixtures of caustic soda plus differing level of soda and biocarbonate were used as reference cleaning compositions. Hot water and caustic soda plus differing levels of soda and or bicarbonate provided the lowest cleaning performance. Formulation B was the most effective formulation tested across the tested temperature range with 97% soil removal at 20° C., increasing to 100% at 60° C. Cleaning Formulation D was somewhat less effective at the lower temperatures, but soil removal increased to 100% at 60° C. The combination of 2% caustic soda and 0.2% Formulation B effectively removed the soil residue at temperatures of 60° C. and above. This indicates that Formulation B-based detergent systems are suitable as start up cleaners. These tests further suggest that Formulation B is a suitable detergent for cleaning fermentation based soils at reduced temperatures.

TABLE 6

Comparative Cleaning Results of Mild Steel Plates at Various Temperatures

| # | | Formulation | % Soil Removed |
|---|---|---|---|
| 1 | Baseline | Water at 80° C. | 39% |
| 2 | | 2% Caustic Soda 80° C. | 83% |
| 3 | NaOH + | 3% Sodium Carbonate at 80° C. | 44% |
| 4 | $CO_2$ | 5% Carb + 4% Bicarb 80° C. | 37% |
| 5 | | 5% Carb + 4% Bicarb + 0.9% NaOH | 51% |
| 6 | NaOH | 0.2% Formulation A | 60% |
| 7 | additives | 0.1% Formulation C pH 9.0 | 63% |
| 8 | Acidic pH | 3% Formulation D at 60° C. Mild Steel | 99% |
| 9 | | 2% Formulation D 60° C. Stainless Steel | 99% |
| 10 | Slightly basic/ | 2% Formulation B pH 9.0 | 100% |
| 11 | near neutral pH | 1% Formulation B [pH 9.0 | 98% |
| 12 | | 0.5% Formulation B pH 9.0 | 96% |

Example 5

Sequestration and Turbidity Tests

Some of the cleaning formulations described herein can be used as sequestrants to stabilize water hardness. Hard water forms deposits that clog plumbing. These deposits, called "scale," are composed mainly of calcium carbonate $CaCO_3$, magnesium hydroxide $Mg(OH)_2$, and calcium sulphate $CaSO_4$. The build-up of scale restricts the flow of water in pipes. In boilers, these deposits impair the flow of heat into water, reducing the heating efficiency and allowing the metal boiler components to overheat. In a pressurized system, this overheating can lead to failure of the boiler. The presence of ions in an electrolyte, in this case, hard water, can also lead to galvanic corrosion, in which one metal will preferentially corrode when in contact with another type of metal, when both are in contact with an electrolyte. These tests demonstrated that heated caustic, in the presence of Formulation B, provided improved sequestration and scale prevention performance.

Water:

Mannheim (Germany) municipal water: 180 mg CaO/L (=321 ppm $CaCO_3$)

Turbidity Test Composition 1:

2% NaOH with addition of $Na_2CO_3$ to simulate a $CO_2$ atmosphere in a fermentation tank.

Turbidity Test Composition 2:

2% NaOH complemented with 0.2% Formulation B and addition of $Na_2CO_3$ to simulate a $CO_2$ atmosphere in a fermentation tank.

Figure 3:
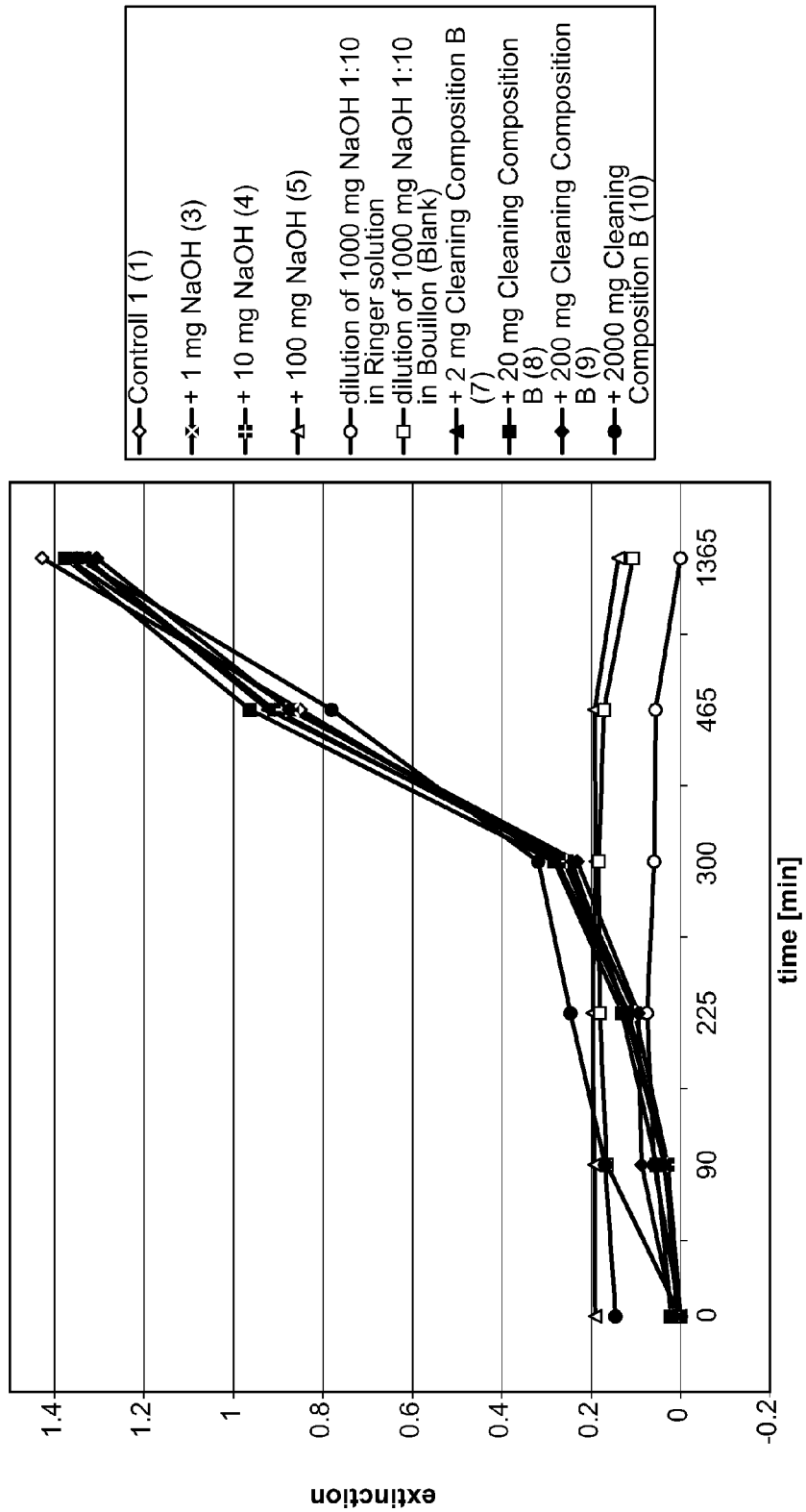
FIG. 3 provides the results of yeast (*S. cerevisiae*) growth assays as described in Example 6.

Lab Test:

Turbidity was measured and is expressed in formazin nephelometric units (FNU). See FIG. 3. Caustic with or without addition of Formulation B was heated up to 80° C. and finally cooled down. For compositions containing Formulation B there was no increase observed on FNU, indicating calcium carbonate precipitation compared to caustic only. Formulation B helps to keep water hardness in solution and to prevent scale deposits.

Conclusions:

Formulation B, provides improved water hardness stabilization as well as an improvement of cleaning performance.

Example 6

Effects of Caustic and Formulation B on Fermentative Yeast

These experiments were used to investigate whether potential residues of cleaning formulations described herein have any impact on the growth or metabolism of a fermentative yeast cell. *Saccaromyces cerevisiae* was selected as a typical member of fermenting yeasts.

Yeast Culture Preparation:

Malt extract agar tubes with an angular surface were used to grow starter cultures. Two globules that were covered with *Saccaromyces cerevisiae* (from a freeze culture collection DSM 1333) were streaked onto an agar surface and incubated at 30° C. for 3 days. Yeast colonies were grown, transferred to liquid growth media and incubated for 15-20 hours at 30° C. A second transfer was conducted into fresh liquid medium. The grown medium was transferred into closed, sterile tubes and centrifuged for 20 minutes at 8000 G. The liquid was decanted and the pellets collected in 10 mL of sterile Ringer solution. A Thoma Hemocytometer was prepared. Cells of 4 squares across were counted. Counted numbers from 4 squares were averaged and cell concentrations were calculated. The concentration of cells in the original mixture=number of cells counted*$10^6$=cells/mL. Dilutions were made to reach final cell concentration of $1\times10^6$/mL in culture medium.

Test Solutions:

Malt extract bouillon; 10×150 mL, 2×150 mL as preculture, 500 mL as Blank, pH≈5.5-5.6. Ringer solution 500 mL (1 tablet to 500 mL of deionized water). Stock solutions were made from sodium hydroxide (NaOH, 50%) and formulation B.

Growth Test:

Suspended cells were added to reach $1\times10^6$/mL in culture medium. Start extinction was measured at 578 nm with help of a spectrophotometer. Flasks were incubated at 30° C. while being stirred at 300 rpm. Every 1 to 2 hours samples were taken and extinctions were measured. If extinction was >1.5, a dilution was made of 1:10 in Ringer solution or pure bouillon. The difference ∂ of extinction to start was calculated. At the end of growth 10 mL was taken of each test batch (while stirring) and transferred it into tubes for centrifugation for 20 minutes at 8000 G. The liquid parts were decanted, pellets were dried at ambient temperature for 1 h and the tubes were weighed to determine the wet weight of cells and the net weight of the pellets.

Discussion and Conclusion:

The supplement of caustic at concentrations above 10 ppm significantly decreased or even inhibited *S. cerevisiae* cell growth while supplements of Formulation B up to 1000 ppm did not cause any inhibition compared to a control without supplements. Some supplements of Formulation B seemed to increase the cell yield rate. Based on the data herein it can be concluded that residues of components of Formulation B (even at relatively high levels) do not appreciably impact yeast cell growth or its metabolism. Thus, there may be no significant need for a final rinse step after a CIP cleaning.

Example 7

The Compatibility of Formulation B with Alpha Amylase

Alpha-amylase is an enzyme that is typically used in starch liquefaction and sugar based fermentation processes. An assay of was alpha-amylase activity conducted with and without Formulation B and differences in enzyme activity were found to be within the uncertainty of the trial. As such, Formulation B is not expected to impact alpha amylase activity during starch liquefaction and sugar-based fermentation processes.

Test Protocol: Liquefaction was carried out by generally accepted protocols. First, a mash was prepared in demineralized water. The pH was set to about 5.5 and the mash concentration was adjusted to about 28% solids in the demineralized water (with calcium if required) until a total weight was calculated. Hot water was used when necessary. Diluted enzyme (0.15 kg/t) was added. Liquefaction began and the mash was heated to 85° C. over about 150 minutes. Starting times were determined when the mash reached a gelatinization point (at approx. 70° C.). Formulation B was found not have a negative impact on the alpha amylase activity during the liquefaction of wheat mash under these standard application conditions.

Example 8

The Addition of Sanitizing Additives to Formulation B

Figure 4:
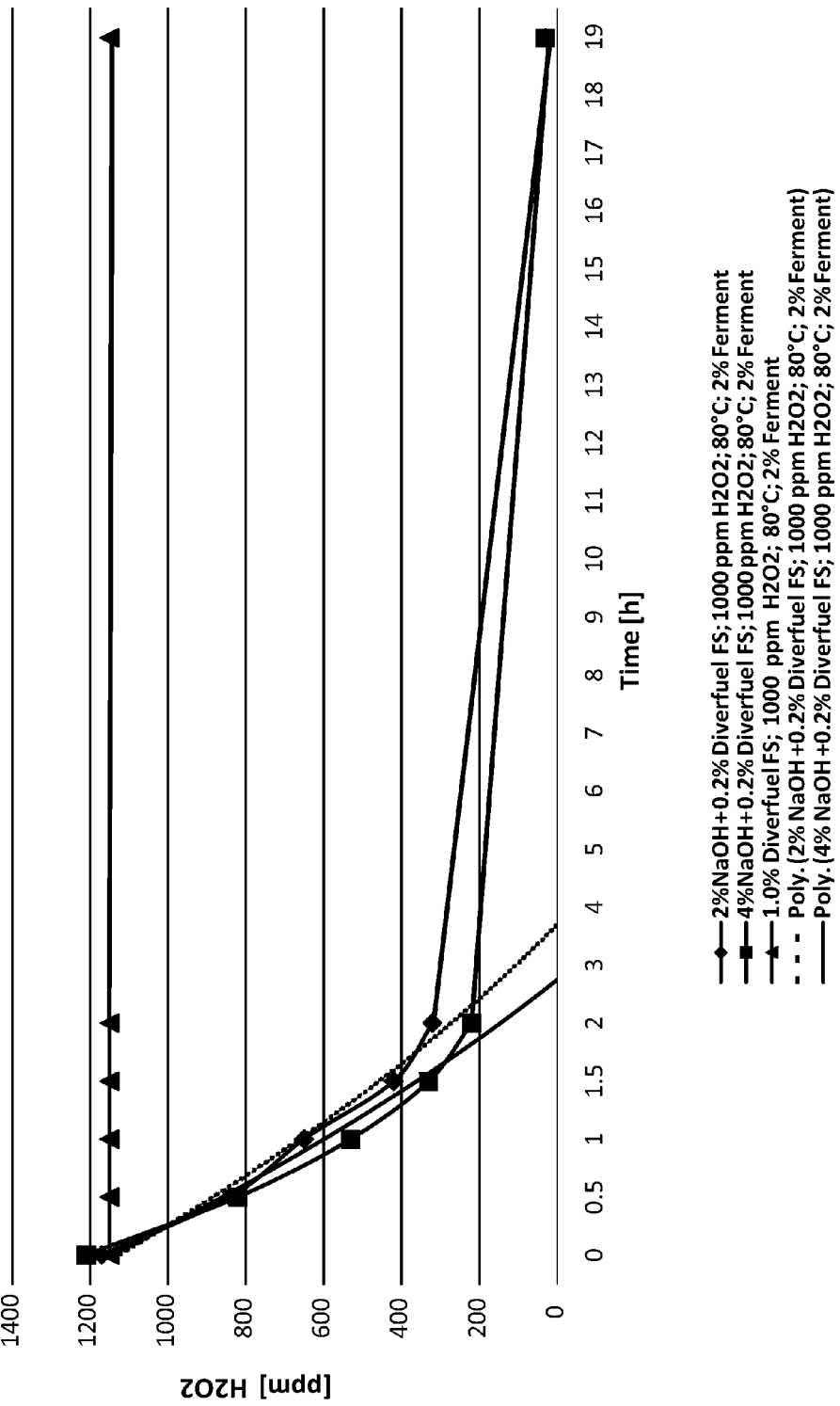
FIG. 4 provides the results of peroxide degradation assays as described in Example 8.
Figure 5:
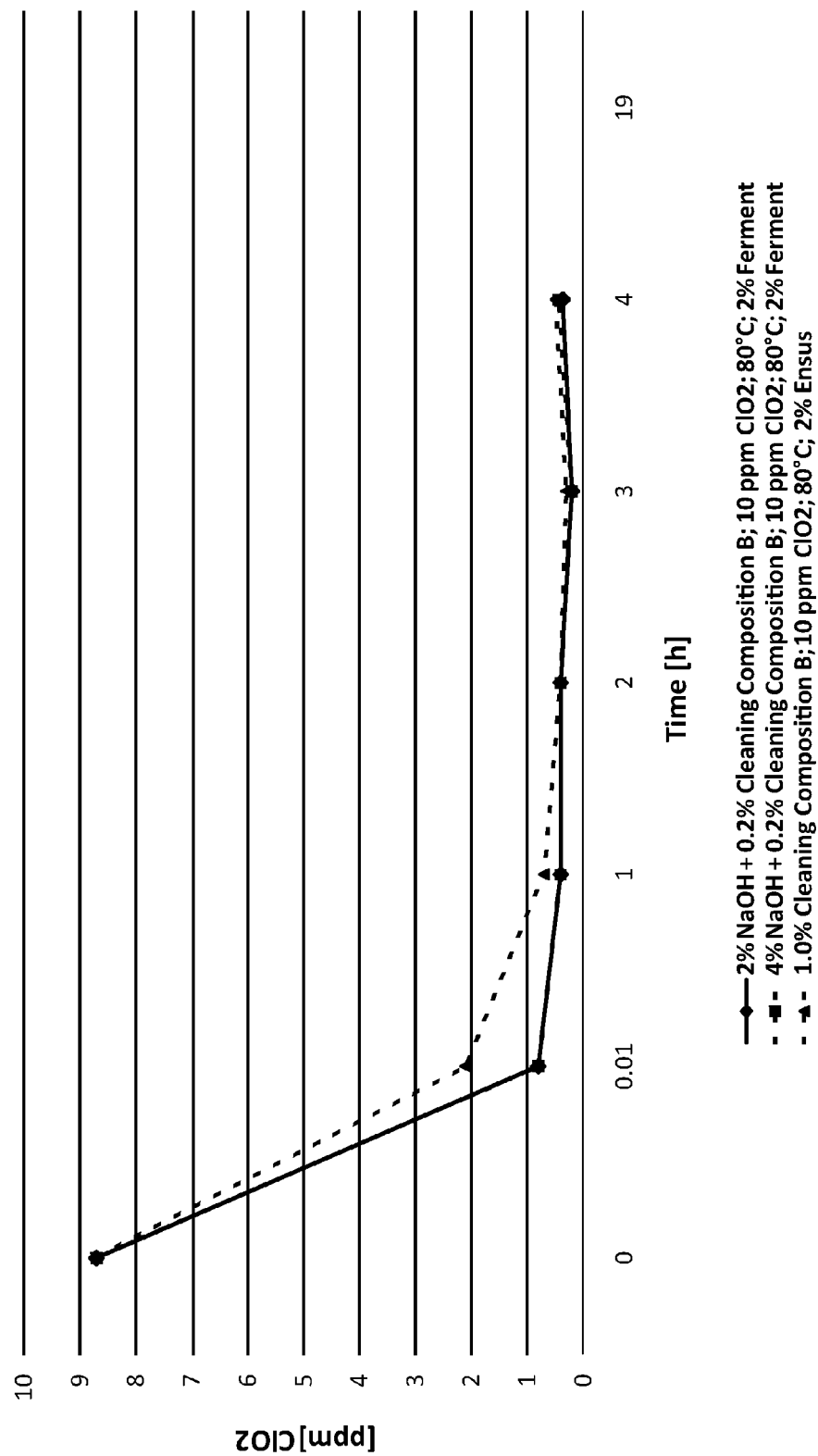
FIG. 5 provides the results of $ClO_2$ degradation assays as described in Example 8.
Figure 6:
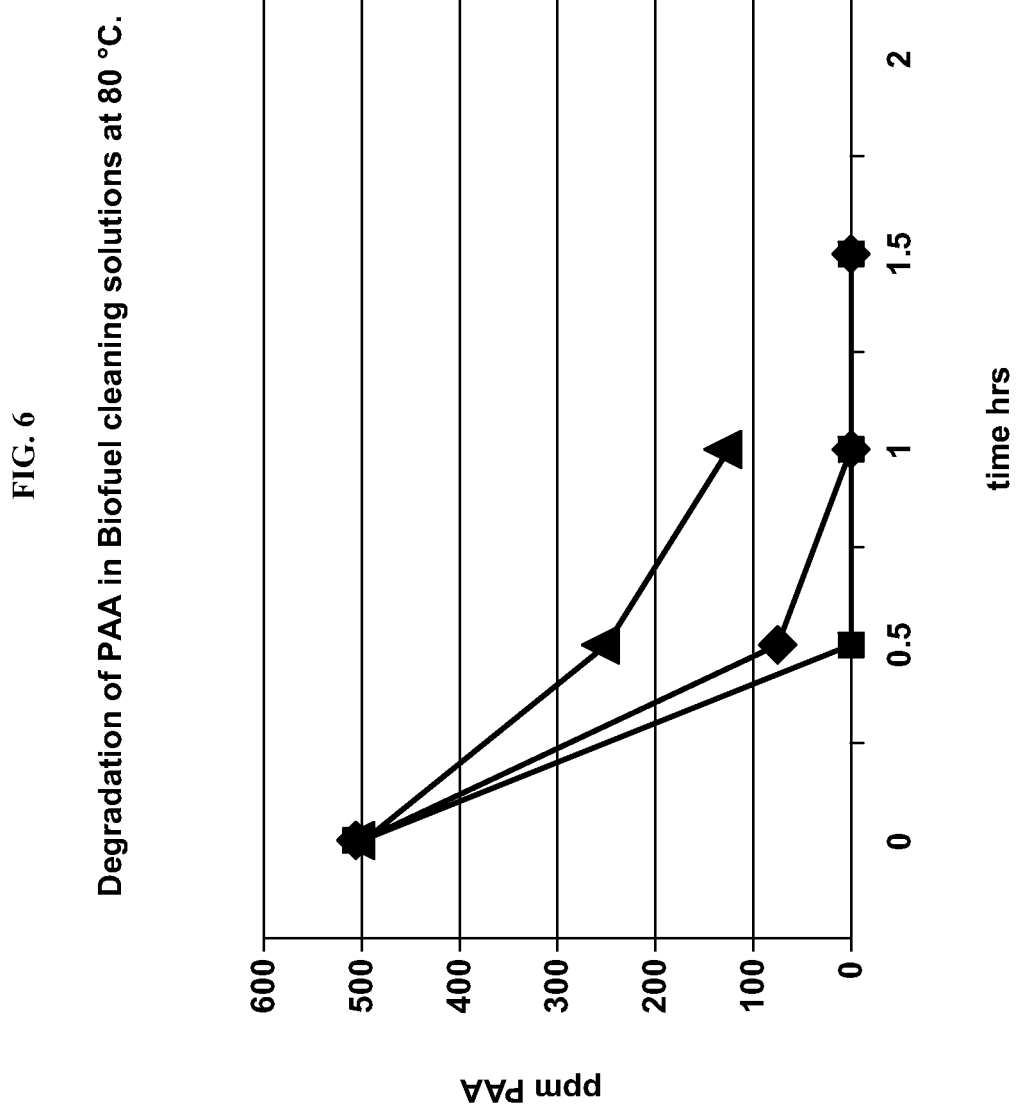
FIG. 6 provides the results of peracetic acid degradation assays as described in Example 8. Diamonds are 2% NaOH+ 0.2% Formulation B ("Form B"); 0.3% Form D; 80° C.; 2% ferment; squares are 4% NaOH+0.2% Form B; 0.3% Formulation D ("Form D"); 80° C.; 2% ferment; triangles are 1% Form B; 0.3% Form D; 80° C.; 2% ferment.

Formulation B was combined with three sanitizing additives hydrogen peroxide (i.e., "peroxide"), peracetic acid (PAA) and chlorine dioxide. See FIGS. 4-6. Testing was conducted at 80° C. to simulate CIP tank conditions. Ferment soil was added to the tests to further simulate real conditions.

Chlorine dioxide (10 ppm) was found to be very unstable. It degraded quickly in minutes, primarily caused by inactivation through ferment soil. 1000 ppm hydrogen peroxide was found to be quite stable in Formulation B and in the presence of ferment soil but of limited stability in high alkaline caustic solutions at 80° C. 0.3% of Formulation E, which is based on peracetic acid (450 ppm active PAA), was found to have limited stability in all tested solutions at 80° C. Peracetic acid demonstrated better stability in Formulation B and ferment soil. In the presence of Formulation B, peracetic acid had a half life concentration>30 minutes) and thus outperformed high alkaline solutions. Stability with Formulation B increased as the temperature dropped.

Example 9

Efficiency Testing Against Lactobacilli and Fermentative Wild Yeasts

Testing was done according to test protocols EN 1276 and EN 1650. Formulation B and Formulation D (a peracetic acid-based formulation) were tested separately and in combination. Formulation B was also tested in combination with hydrogen peroxide. Tests were run at 20°, 40° C. and 60° C. in the presence of 1% ferment soil at contact times of 10, 20 and 30 minutes. Results are shown in Tables 7 and 8. Kill rates are expressed as log reductions.

TABLE 7

Efficiency against fermentative wild yeasts
(kill is expressed as log reduction)

| Formulation | Strain | Time | 20° C. | 40° C. | 60° C. |
|---|---|---|---|---|---|
| 1% Formulation B | *Saccharomyces diastaticcus* | 10 minutes | 0.37 | 0.14 | 3.01 |
| | | 20 minutes | 0.24 | −0.05 | 3.74 |
| | | 30 minutes | −0.10 | −0.05 | 3.66 |
| | *Dekkera bruxellensis* | 10 minutes | 0.06 | 0.06 | 3.20 |
| | | 20 minutes | −0.01 | −0.02 | 3.77 |
| | | 30 minutes | −0.12 | 0.00 | 4.06 |
| | *Dekkera anomala* | 10 minutes | 0.28 | 0.12 | 3.33 |
| | | 20 minutes | 0.14 | −0.01 | 3.91 |
| | | 30 minutes | 0.06 | 0.05 | 4.28 |
| 1% Formulation B + 0.15% Formulation D | *Saccharomyces diastaticcus* | 10 minutes | 2.60 | 2.51 | |
| | | 20 minutes | >4.39 | >4.39 | |
| | | 30 minutes | >4.39 | >4.39 | |
| | *Dekkera bruxellensis* | 10 minutes | >4.42 | >4.42 | |
| | | 20 minutes | >4.42 | >4.42 | |
| | | 30 minutes | >4.42 | >4.42 | |
| | *Dekkera anomala* | 10 minutes | >4.48 | >4.48 | |
| | | 20 minutes | >4.48 | >4.48 | |
| | | 30 minutes | >4.48 | >4.48 | |
| 1% Formulation B + 0.3% Formulation D | *Saccharomyces diastaticcus* | 10 minutes | 3.85 | 3.66 | |
| | | 20 minutes | >4.39 | >4.39 | |
| | | 30 minutes | >4.39 | >4.39 | |
| | *Dekkera bruxellensis* | 10 minutes | >4.42 | >4.42 | |
| | | 20 minutes | >4.42 | >4.42 | |
| | | 30 minutes | >4.42 | >4.42 | |
| | *Dekkera anomala* | 10 minutes | >4.48 | >4.48 | |
| | | 20 minutes | >4.48 | >4.48 | |
| | | 30 minutes | >4.48 | >4.48 | |
| 2% Formulation D | *Saccharomyces diastaticcus* | 10 minutes | >4.35 | >4.35 | >4.35 |
| | | 20 minutes | >4.35 | >4.35 | >4.35 |
| | | 30 minutes | >4.35 | >4.35 | >4.35 |
| | *Dekkera bruxellensis* | 10 minutes | >4.36 | >4.36 | >4.36 |
| | | 20 minutes | >4.36 | >4.36 | >4.36 |
| | | 30 minutes | >4.36 | >4.36 | >4.36 |
| | *Dekkera anomala* | 10 minutes | >4.49 | >4.49 | >4.49 |
| | | 20 minutes | >4.49 | >4.49 | >4.49 |
| | | 30 minutes | >4.49 | >4.49 | >4.49 |

TABLE 8

Efficiency against *Lactobacillus brevis* (kill is expressed as log reduction)

| Product Concentration | Time | 20° C. | 40° C. | 60° C. |
|---|---|---|---|---|
| 1% Formulation B | 10 minutes | 0.06 | 0.11 | 4.34 |
| | 20 minutes | 0.09 | 0.11 | 5.09 |
| | 30 minutes | 0.04 | 0.24 | >5.25 |
| 1% Formulation B + | 10 minutes | 0.10 | 0.14 | 5.09 |
| 1000 ppm H$_2$O$_2$ | 20 minutes | 0.16 | 0.22 | 5.31 |
| | 30 minutes | 0.15 | −0.01 | >5.35 |
| 1% Formulation B + | 10 minutes | 0.40 | 0.80 | >5.35 |
| 5000 ppm H$_2$O$_2$ | 20 minutes | 1.90 | 5.35 | >5.35 |
| | 30 minutes | 5.35 | 5.35 | >5.35 |
| 1% Formulation B + | 10 minutes | 5.35 | 5.35 | >5.35 |
| 0.3% Formulation D | 20 minutes | 5.35 | 5.35 | >5.35 |
| | 30 minutes | 5.35 | 5.35 | >5.35 |

Formulation B was shown to be relatively ineffective against tested yeasts and *Lactobacillus* strains, whereas Formulation D exhibited effective kill at 2% against tested wild yeast strains at all temperatures and contact times. At 20° C. and 40° C., 0.28% peroxide (1000 ppm) was ineffective on Lactobacilli. The higher kill rate at 60° C. is mainly due to temperature. 1.4% Peroxide (5000 ppm) became effective against Lactobacilli at 40° C. and 20 minute contact times. 0.3% PAA (450 ppm) was very effective on Lactobacilli and wild yeasts at all temperatures for 20 minutes or longer. 0.15% PAA (225 ppm PAA) was very effective on wild yeasts at all temperatures for 20 minutes or longer. 0.3% PAA (PAA), in combination with 1% Formulation B, was very effective on relevant Lactobacilli and wild yeasts at ambient temperature for 20 minutes or longer.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A method of cleaning, sanitizing, or disinfecting, wherein the method comprises:
    contacting a soiled substrate with a cleaning, sanitizing, or disinfecting composition, such that at least a portion of the soil is removed from the substrate;
    wherein the cleaning, sanitizing, or disinfecting composition consists essentially of tripolyphosphoric acid or a salt thereof and optionally one or more food grade agents selected from the group consisting of carbonate, peroxyacetic acid or salt thereof, and hydrogen peroxide; and wherein the method does not include contacting the substrate with hydroxide, is effluent neutral, and is a clean-in-place (CIP) or sanitize-in-place (SIP) method.

2. The method of claim 1 comprising recycling the cleaning, sanitizing, or disinfecting composition for further use, wherein the composition comprises solids that are separated before further use of the composition in cleaning, sanitizing, or disinfecting soiled substrates.

3. The method of claim 2 wherein the separated solids are added to an animal feedstock.

4. The method of claim 1, wherein the cleaning, sanitizing, or disinfecting composition is added to an animal feedstock.

5. The method of claim 4 wherein the cleaning, sanitizing, or disinfecting composition is concentrated before being added to an animal feedstock.

6. The method of claim 1, wherein the soil on the soiled substrate comprises a residue of a grain, dairy product, alcoholic beverage, non-alcoholic beverage, fruit, vegetable, meat, animal food, soiled dish residue, an industrial fermentation product, algae, biofuel, pharmaceutical, nutritional supplement, cosmetic, or a combination of any two or more thereof.

7. The method of claim 1, wherein the substrate is selected from the group consisting of a brewing apparatus for an alcoholic beverage, apparatus for producing a non-alcoholic beverage, apparatus for producing a dairy product, food-processing apparatus, industrial fermentation apparatus, apparatus for producing biofuel, pharmaceutical processing apparatus, cosmetic processing apparatus, apparatus for producing a nutritional supplement, and a dish-washing apparatus.

8. A method of cleaning, sanitizing, or disinfecting wherein the method consists of:
   contacting a soiled substrate with a cleaning, sanitizing, or disinfecting composition, such that at least a portion of the soil is removed from the substrate; and
   optionally rinsing the substrate one or more times with water;
   wherein the cleaning, sanitizing, or disinfecting composition consists of tripolyphosphoric acid or salt thereof, water, and optionally one or more food grade agents selected from the group consisting of hydroxide, carbonate, hydrogen peroxide, and peracetic acid or a salt thereof; and
   wherein the method is effluent neutral, and is a clean-in-place (CIP) or sanitize-in-place (SIP) method.

9. The method of claim 8 wherein carbonate is formed in the cleaning, sanitizing, or disinfecting composition, and the carbonate does not substantially reduce the cleaning, sanitizing, or disinfecting efficacy of the cleaning, sanitizing, or disinfecting composition.

10. The method of claim 8 wherein carbonate is formed in the cleaning, sanitizing, or disinfecting composition, and the carbonate does not substantially reduce activity of an enzyme used during liquefaction or fermentation of sugar-based materials during the production of an alcohol.

11. The method of claim 8, wherein the cleaning, sanitizing, or disinfecting composition consists of about 0.01-5.0 wt. % potassium tripolyphosphoric acid, 0-2.0 wt. % sodium hydroxide, 0-2.0 wt. % sodium carbonate, 0-2.0 wt. % hydrogen peroxide, 0-2.0 wt. % peracetic acid, and water.

12. A method of cleaning, sanitizing, or disinfecting, wherein the method comprises:
    contacting a soiled substrate with a cleaning, sanitizing, or disinfecting composition, such that at least a portion of the soil is removed from the substrate;
    wherein the cleaning, sanitizing, or disinfecting composition consists essentially of a phosphoric acid or a salt thereof, one or more organic acids or a salt thereof, and a hydrotrope agent; and
    wherein the method does not include contacting the substrate with hydroxide, is effluent neutral, and is a clean-in-place (CIP) or sanitize-in-place (SIP) method.

13. The method of claim 8, wherein the soiled substrate is a fermentation apparatus for the fermentation of a sugar-based material into a biofuel and the biofuel is selected from the group consisting of ethanol, butanol, biodiesel, biogas, and syngas.

14. The method of claim 12, wherein the hydrotrope agent is selected from the group consisting of benzene sulfonates, naphthalene sulfonates, alkyl benzene sulfonates, naphthalene sulfonates, alkyl sulfonates, alkyl sulfates, alkyl diphenyloxide disulfonates, and phosphate ester hydrotropes.

15. The method of claim 12 wherein the phosphoric acid is tripolyphosphoric acid or a salt thereof.

16. A method of cleaning, sanitizing, or disinfecting, wherein the method comprises:
    contacting a soiled substrate with a cleaning, sanitizing, or disinfecting composition, such that at least a portion of the soil is removed from the substrate;
    wherein the cleaning, sanitizing, or disinfecting composition consists essentially of about 0.01-5.0 wt. % sodium and/or potassium tripolyphosphate, 0-2.0 wt. % sodium carbonate, 0.01-2.0 wt. % hydrogen peroxide, 0.01-2.0 wt. % peracetic acid, and water; and
    wherein the method does not include contacting the substrate with hydroxide, is effluent neutral, and is a clean-in-place (CIP) or sanitize-in-place (SIP) method.

* * * * *